United States Patent
Yanagimoto et al.

(10) Patent No.: US 10,961,227 B2
(45) Date of Patent: Mar. 30, 2021

(54) PIGMENT DISPERSING AGENT, PIGMENT COMPOSITION, AND PIGMENT COLORING AGENT

(71) Applicant: DAINICHISEIKA COLOR & CHEMICALS MFG. CO., LTD., Tokyo (JP)

(72) Inventors: Hiromitsu Yanagimoto, Tokyo (JP); Shuwa Ozako, Tokyo (JP)

(73) Assignee: DAINICHISEIKA COLOR & CHEMICALS MFG. CO., LTD., Tokyo (JP)

( * ) Notice: Subject to any disclaimer, the term of this patent is extended or adjusted under 35 U.S.C. 154(b) by 0 days.

(21) Appl. No.: 16/755,802

(22) PCT Filed: Oct. 25, 2018

(86) PCT No.: PCT/JP2018/039662
§ 371 (c)(1),
(2) Date: Apr. 13, 2020

(87) PCT Pub. No.: WO2019/082967
PCT Pub. Date: May 2, 2019

(65) Prior Publication Data
US 2020/0377480 A1 Dec. 3, 2020

(30) Foreign Application Priority Data

Oct. 27, 2017 (JP) .............................. JP2017-207843
Oct. 27, 2017 (JP) .............................. JP2017-207844

(51) Int. Cl.
| | |
|---|---|
| *C07D 403/12* | (2006.01) |
| *C08K 5/3492* | (2006.01) |
| *C09B 67/20* | (2006.01) |
| *C09D 11/037* | (2014.01) |
| *C09D 17/00* | (2006.01) |
| *D06P 1/642* | (2006.01) |

(52) U.S. Cl.
CPC .......... *C07D 403/12* (2013.01); *C08K 5/3492* (2013.01); *C09B 67/0066* (2013.01); *C09D 11/037* (2013.01); *C09D 17/003* (2013.01); *D06P 1/6426* (2013.01)

(58) Field of Classification Search
CPC ................ C07D 403/12; C08K 5/3492; C09B 67/0066; C09D 11/037; C09D 17/003; D06P 1/6426
USPC ........................................................ 524/100
See application file for complete search history.

(56) References Cited

U.S. PATENT DOCUMENTS

2010/0315733 A1* 12/2010 Saikatsu ................. C09D 7/45
                                                       359/891
2015/0293282 A1  10/2015 Takishita et al.
2018/0196177 A1   7/2018 Takishita et al.

FOREIGN PATENT DOCUMENTS

| JP | 02-216102   | 8/1990 |
| JP | 04-015265   | 3/1992 |
| JP | 09-95625    | 4/1997 |
| JP | 2819512     | 8/1998 |
| JP | 2000-066018 | 3/2000 |
| JP | 2001-240780 | 9/2001 |

(Continued)

OTHER PUBLICATIONS

STIC search results for 16755802, Sep. 29, 2020. (Year: 2020).*

(Continued)

*Primary Examiner* — Hui H Chin
(74) *Attorney, Agent, or Firm* — Hamre, Schumann, Mueller & Larson, P.C.

(57) ABSTRACT

The present invention provides a pigment dispersant: that is capable of remarkably ameliorating fluidity of a liquid product, such as an ink or a paint, which contains particles of a pigment, such as a black azo pigment, in a dispersed state; that can suppress aggregation of pigment particles; that prevents occurrence of foreign substances; and that is capable of producing a colored article excellent in optical density. Provided is a pigment dispersant being a compound represented by the following formula (1).

(1)

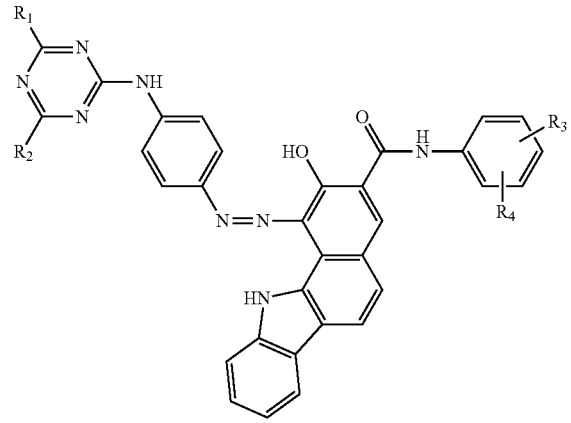

wherein $R_1$ and $R_2$ each independently represent a group obtained by eliminating one hydrogen atom from an amino group of an amine compound containing a basic nitrogen atom, and $R_3$ and $R_4$ each independently represent a hydrogen atom, a halogen atom, an alkyl group, an alkoxy group, or a hydroxy group.

6 Claims, No Drawings

(56) References Cited

FOREIGN PATENT DOCUMENTS

| JP | 2002-055224 | 2/2002 |
|----|-------------|--------|
| JP | 2002-341332 | 11/2002 |
| JP | 3543501 | 4/2004 |
| JP | 2005-084111 | 3/2005 |
| JP | 2008-223007 | 9/2008 |
| JP | 4338479 | 7/2009 |
| JP | 2009-197213 | 9/2009 |
| JP | 2010-065062 | 3/2010 |
| JP | 2014-130173 | 7/2014 |

OTHER PUBLICATIONS

International Preliminary Report on Patentability, issued in the corresponding PCT application No. PCT/JP2018/039662, dated May 7, 2020, 10 pages (including translation).
Australian Examination Report, issued in the corresponding Australian patent application No. 2018357511, dated May 19, 2020, 3 pages.
Chinese Office Action, issued in the corresponding Chinese patent application No. 201880070182.6, dated Sep. 2, 2020, 14 pages (including translation).
International Search Report, issued in the corresponding PCT application No. PCT/JP2018/039662, dated Jan. 29, 2019, 5 pages.

* cited by examiner

PIGMENT DISPERSING AGENT, PIGMENT COMPOSITION, AND PIGMENT COLORING AGENT

TECHNICAL FIELD

The present invention relates to a pigment dispersant, a pigment composition, and a pigment colorant. In more detail, the present invention relates a pigment dispersant to be compounded in printing inks (such as an offset ink and a gravure ink), various paints, plastics, pigment printing agents, electrophotographic dry toners, electrophotographic wet toners, inkjet recording inks, thermal transfer recording inks, color filter resists, writing tool inks, and the like.

BACKGROUND ART

It is generally difficult to mix and disperse a pigment (particles) stably in a vehicle of a paint, a gravure ink, an offset ink, or the like. For example, fine pigment particles once dispersed in a vehicle tend to aggregate in the vehicle. When the pigment particles aggregate, the viscosity of the vehicle increases. In addition, when a vehicle containing pigment particles which are in an aggregation state is used, various problems that the colorability of an ink or a paint is lowered, the gloss of a coating film is lowered, etc. are liable to occur. Among the pigments, it is particularly difficult to mix and disperse a black pigment stably.

As black pigments which have been used as a colorant for paints, printing inks, plastics, and the like, carbon black-based pigments, iron oxide-based pigments, and the like are generally used. These black pigments exhibit a black color by absorbing all the rays of light, including a visible light region in the sunlight.

The sunlight is composed of electromagnetic waves, and the light in a wavelength region of approximately from 380 to 780 nm forms visible light rays. Therefore, the black color is exhibited only by absorbing all the visible light rays. The light in a wavelength region of 0.8 μm to 2.5 μm (800 nm to 2,500 nm), which is a wavelength region on the longer wavelength side of the visible light rays and is between a visible light ray region and an infrared ray region, is called near infrared rays. The carbon black-based pigments also absorb these near infrared rays. It is to be noted that, among the near infrared rays, it is considered to be the light in a wavelength region of 800 nm to 1,400 nm that has a particularly large degree of contribution to heat in a wavelength region of the sunlight.

As described above, a black pigment such as a carbon black-based pigment also absorbs the near infrared rays in the wavelength region of 800 nm to 1,400 nm, which have a large degree of contribution to heat. Therefore, there has been a problem that when an article colored with a black pigment is exposed to the sunlight, the temperature of the article thereby easily rises. As an article colored with a black pigment, there are a large number of sophisticated products such as a black matrix (hereinafter, also simply written as "BM") that constitutes a color filter (hereinafter, also simply written as "CF"). Therefore, various studies have been investigated on: a black pigment; a colorant composition for coloring various articles into black; and the like, the temperature of which does not rise even when they are exposed to the sunlight.

In Patent Literature 1, a black azo pigment that exhibits a black color by absorbing visible light rays and reflects infrared rays, the black azo pigment having an azomethine group, is disclosed. In addition, since this black azo pigment reflects infrared rays, obtaining an article the temperature of which does not rise excessively even by direct sunlight or the like by coloring the article with this black azo pigment; and the like are proposed.

By the way, with remarkable progress in information devices in recent years, a liquid color display (hereinafter, also simply written as "LCD") is applied as an information-displaying member to a large number of information display-related devices. With the application of the liquid color display to the information display-related devices, improvements in display quality of LCD and cost reduction of LCD are desired. Therefore, having more excellent product quality in terms of color properties and optical properties, such as definition, color density, light transparency, and contrast, is required also in CF to be mounted on LCD.

In CF, respective pixels of R (red), G (green), and B (blue) are arranged in the form of a stripe, a mosaic, or a triangle, and in order to shield unwanted light, BM in the form of a grid is formed around each pixel. A picture is formed by irradiating CF from the back with light of a back light and developing colors through additive color mixture with transmitted light from each pixel of R, G, and B. A red pigment, a green pigment, a blue pigment, a yellow pigment, a violet pigment, and the like are used for chromatic (RGB) pixels, and these are each improved. In addition, a light-shielding material that constitutes BM is shifting from a conventional metallic chrome film to a resin film using a black pigment in order to meet increases in substrate size, reductions in environmental load, and the like.

In addition, various improvements are proposed also in the method of displaying pixels in CF, and concomitantly with the improvements, light-shielding black pigments for use in BM are also improved. For example, an in-plane switching method (IPS method), in which pixels are displayed by applying an electric field in parallel with a substrate to convert a liquid crystal layer in order to widen the viewing angle, is proposed. In addition, a black-matrix-on-array method (BOA method), in which BM is formed on a thin film transistor (TFT), and a color filter-on-array method (COA method) are proposed. In these methods, the aperture ratio is made high, and therefore a pixel area can be expanded. Further, the efficiency of a sticking process is improved, and therefore an operation process can also be streamlined.

For example, to widen a viewing angle more in the IPS method, it is considered that a space (cell gap) between the substrates that hold a liquid crystal layer therebetween is required to be kept constant with high accuracy. However, it is difficult to adjust the cell gap uniformly in a conventional system in which a bead-like spacer is sprayed. Therefore, as a method of adjusting the cell gap uniformly, methods such as thickening BM itself and thickening by laminating a resin on BM, the resin supporting the space of a coloring layer, a photoresist layer, and the like, are proposed. Further, in these methods, a conventional bead-like spacer is not used, and therefore it is considered that deterioration in the display quality due to scattering and transmission of light can be suppressed (Patent Literatures 2 and 3).

Methods such as the IPS method, the BOA method, and the COA method are the methods of forming BM on an active element such as TFT, and therefore there is a possibility that the active element malfunctions when BM is not electrically insulating. A carbon black-based pigment which is conventionally used as a light-shielding black pigment has a low electric resistance, and therefore it cannot be said that the carbon black-based pigment is suitable as a black pigment to be applied to the above-described methods.

Accordingly, a light-shielding black pigment that is more excellent in electric insulation is desired.

To meet such desire, for example, a black pigment for BM, wherein carbon black in which the amount of oxygen is specified is covered with a highly insulating resin film to improve the electric insulation, is proposed (Patent Literature 4). In addition, applying BM to the COA method, the BM formed using insulating carbon black selected by measuring the volume resistance value or using carbon black covered with a resin to improve the electric insulation, is proposed (Patent Literature 5). However, a carbon black-based pigment is a material which has electric conductivity inherently, and therefore it has been difficult to secure sufficient insulation even when the carbon black-based pigment is subjected to resin coating or the like.

On the other hand, using a black azo pigment having an azomethine group, the black pigment proposed in Patent Literature 1, is proposed in order to secure the insulation of BM (Patent Literature 6). However, it has been difficult to mix and disperse the black azo pigment proposed in Patent Literature 1 stably in a vehicle. Fine pigment particles once dispersed in a vehicle tend to aggregate in the vehicle. The viscosity of the vehicle in which pigment particles have aggregated increases. In addition, when a vehicle containing pigment particles which have aggregated is used, a problems such as that the colorability of an ink or a paint is lowered, the gloss of a coating film is lowered, or the optical density is insufficient as a light-shielding material for forming BM has occurred.

In order to disperse particles of a pigment, such as a black azo pigment having an azomethine group, stably in a dispersion medium, a method of using a pigment derivative as a dispersant; a method of using a pigment treated with a pigment derivative; and the like are proposed. Specifically, when a phthalocyanine-based pigment, such as PB 15:6, is used, using as a pigment dispersant a substituted derivative of phthalocyanine is proposed (Patent Literature 7). In addition, when an anthraquinone-based pigment, such as PR 177, is used, using as a pigment dispersant a substituted derivative of anthraquinone is proposed (Patent Literature 8). Further, when a diketopyrrolopyrrole-based pigment, such as PR 254, is used, using as a pigment dispersant a substituted derivative of diketopyrrolopyrrole is proposed (Patent Literature 8).

CITATION LIST

Patent Literature

Patent Literature 1: Japanese Patent Publication No. 4-15265
Patent Literature 2: Japanese Patent Laid-Open No. 2000-66018
Patent Literature 3: Japanese Patent Laid-Open No. 2002-341332
Patent Literature 4: Japanese Patent No. 3543501
Patent Literature 5: Japanese Patent No. 4338479
Patent Literature 6: Japanese Patent No. 2819512
Patent Literature 7: Japanese Patent Laid-Open No. 2002-55224
Patent Literature 8: Japanese Patent Laid-Open No. 2001-240780

SUMMARY OF INVENTION

Technical Problem

However, it has been difficult to disperse the black azo pigment having an azomethine group, the black azo pigment proposed in Patent Literature 1, stably in a medium even if the pigment derivatives proposed in Patent Literatures 7 and 8 are used. In addition, there has also been a problem that the optical density of a black color is lowered because the color tone of the pigment derivatives proposed in Patent Literatures 7 and 8 is not black.

The present invention has been completed in view of such problems of the conventional techniques, and an object of the present invention is to provide a pigment dispersant: that is capable of remarkably ameliorating fluidity of a liquid product, such as an ink or a paint, which contains particles of a pigment, such as a black azo pigment, in a dispersed state; that can suppress aggregation of pigment particles; that prevents occurrence of foreign substances; and that is capable of producing a colored article excellent in optical density. Another object of the present invention is to provide a pigment composition and a pigment colorant which are each obtained using the above-described pigment dispersant.

Solution to Problem

That is, according to the present invention, a pigment dispersant described below is provided.

[1] A pigment dispersant (hereinafter, also written as "the first pigment dispersant") being a compound represented by the following formula (1).

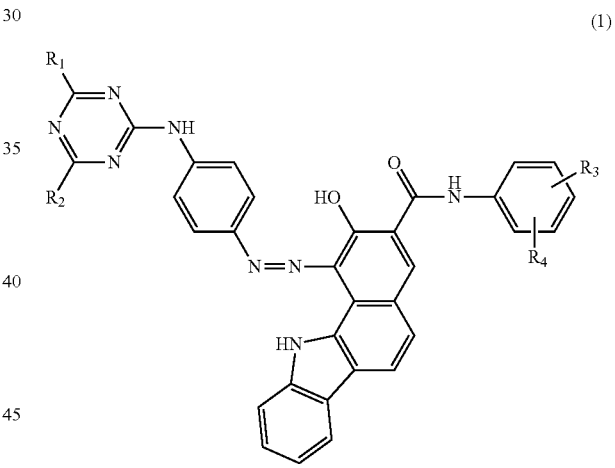

wherein $R_1$ and $R_2$ each independently represent a group obtained by eliminating one hydrogen atom from an amino group of an amine compound having a chain or cyclic aliphatic hydrocarbon group having 2 to 30 carbon atoms or an aromatic hydrocarbon group, the amine compound containing a basic nitrogen atom and optionally containing a hetero atom other than a nitrogen atom, and $R_3$ and $R_4$ each independently represent a hydrogen atom, a halogen atom, an alkyl group, an alkoxy group, or a hydroxy group.

[2] The pigment dispersant according to [1], wherein $R_1$ and $R_2$ in the formula (1) each independently represent a group represented by the following formula (2) or (3).

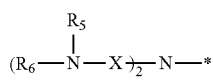

(3)

wherein * shows a position of bonding with a triazine ring; each X independently represents an alkylene group having 1 to 4 carbon atoms; and $R_5$ and $R_6$ each independently represent a hydrogen atom or an alkyl group having 1 to 6 carbon atoms, $R_5$ and $R_6$ optionally bond to each other to form a cyclic structure, and the cyclic structure optionally contains a hetero atom.

Further, according to the present invention, a pigment dispersant described below is provided.

[3] A pigment dispersant (hereinafter, also written as "the second pigment dispersant") being a compound represented by the following formula (4).

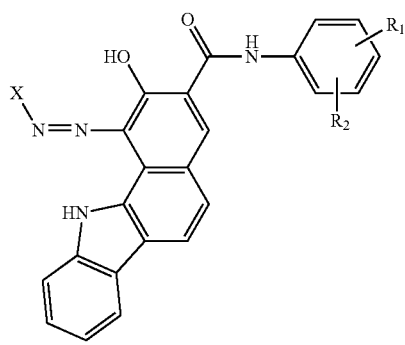

(4)

wherein X represents an aromatic group having at least one sulfonate group, and $R_1$ and $R_2$ each independently represent a hydrogen atom, a halogen atom, an alkyl group, an alkoxy group, or a hydroxy group.

[4] The pigment dispersant according to [3], wherein X in the formula (4) represents a group represented by any one of the following formulas (5) to (7).

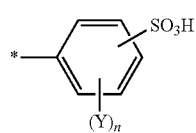

(5)

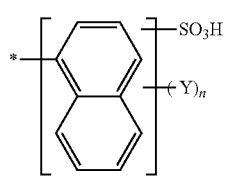

(6)

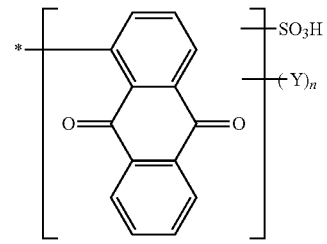

(7)

wherein * shows a position of bonding with a nitrogen atom, each Y independently represents a halogen atom, and n represents a number of 0 to 2.

In addition, according to the present invention, a pigment composition described below is provided.

[5] A pigment composition comprising: a pigment; and the pigment dispersant according to any one of [1] to [4].

[6] The pigment composition according to [5], wherein a content of the pigment dispersant based on 100 parts by mass of the pigment is 0.5 to 40 parts by mass.

Further, according to the present invention, a pigment colorant described below is provided.

[7] A pigment colorant comprising: the pigment composition according to [5] or [6]; and a film-forming material.

[8] The pigment colorant according to [7] for displaying images, recording images, a gravure printing ink, a writing ink, a plastic, pigment printing, a paint, or a black matrix of a color filter.

Advantageous Effects of Invention

According to the present invention, a pigment dispersant: that is capable of remarkably ameliorating fluidity of a liquid product, such as an ink or a paint, which contains particles of a pigment, such as a black azo pigment, in a dispersed state; that can suppress aggregation of pigment particles; that prevents occurrence of foreign substances; and that is capable of producing a colored article excellent in optical density can be provided. In addition, according to the present invention, a pigment composition and a pigment colorant which are each obtained using the above-described pigment dispersant can be provided.

DESCRIPTION OF EMBODIMENTS

<Pigment Dispersant>

(First Pigment Dispersant)

Hereinafter, details on the present invention will be described giving preferred embodiments as examples. One of the main characteristics of a pigment dispersant (the first pigment dispersant) of the present invention is that it is a compound represented by the following formula (1). The pigment dispersant of the present invention having such a characteristic has an excellent affinity to various pigments and can suitably be used as a pigment dispersant for dispersing various pigments irrespective of organic and inorganic pigments. In addition, the pigment dispersant of the present invention has an excellent pigment-dispersing effect and therefore can be used as a material for preparing pigment colorants for various uses.

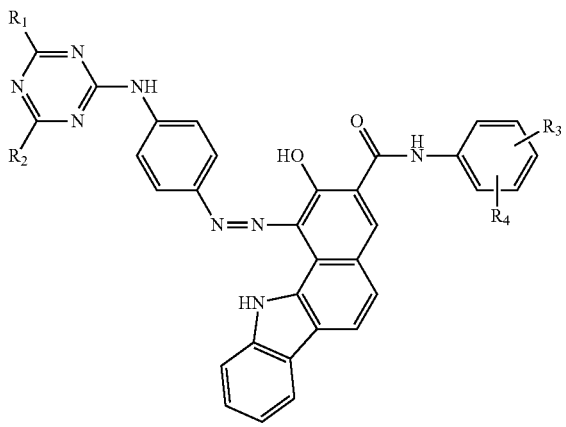

(1)

wherein $R_1$ and $R_2$ each independently represent a group obtained by eliminating one hydrogen atom from an amino group of an amine compound having a chain or cyclic aliphatic hydrocarbon group having 2 to 30 carbon atoms or an aromatic hydrocarbon group, the amine compound containing a basic nitrogen atom and optionally containing a hetero atom other than a nitrogen atom, and $R_3$ and $R_4$ each independently represent a hydrogen atom, a halogen atom, an alkyl group, an alkoxy group, or a hydroxy group.

In formula (1), $R_1$ and $R_2$ each independently represent a group obtained by eliminating one hydrogen atom from an amino group of a particular amine compound. This particular amine compound is a compound having a chain or cyclic aliphatic hydrocarbon group having 2 to 30 carbon atoms or an aromatic hydrocarbon group, the amine compound containing a basic nitrogen atom and optionally containing a hetero atom other than a nitrogen atom. Specific examples of the particular amine compound include N,N-dimethylaminomethylamine, N,N-diethylaminomethylamine, N,N-dipropylaminomethylamine, N,N-dibutylaminomethylamine, N,N-dimethylaminoethylamine, N,N-diethylaminoethylamine, N,N-dipropylaminoethylamine, N,N-dibutylaminoethylamine, N,N-dimethylaminopropylamine, N,N-diethylaminopropylamine, N,N-dipropylaminopropylamine, N,N-dimethylaminobutylamine, N,N-diethylaminobutylamine, N,N-dipropylaminobutylamine, N,N-dibutylaminobutylamine, N,N-dimethylaminolaurylamine, N,N-diethylaminolaurylamine, N,N-dibutylaminolaurylamine, N,N-dimethylaminostearylamine, N,N-diethylaminostearylamine, N,N-diethanolaminoethylamine, N,N-diethanolaminopropylamine, N-(3-aminopropyl)cyclohexylamine, N-(3-aminopropyl)morpholine, 1-(3-aminopropyl)-2-pipecholine, N-aminopropylpyrrolidine, N,N-diethylaminoethoxypropylamine, N,N,N'',N''-tetramethyldiethylenetriamine, N,N,N'',N''-tetraethyldiethylenetriamine, N,N,N'',N''-tetra(n-propyl)diethylenetriamine, N,N,N'',N''-tetra(i-propyl)diethylenetriamine, N,N,N'',N''-tetra(n-butyl)diethylenetriamine, N,N,N'',N''-tetra(i-butyl)diethylenetriamine, N,N,N'',N''-tetra(t-butyl)diethylenetriamine, 3,3'-iminobis(N,N-dimethylpropylamine), 3,3'-iminobis(N,N-diethylpropylamine), 3,3'-iminobis(N,N-di(n-propyl)propylamine), 3,3'-iminobis(N,N-di(n-butyl)propylamine), 3,3'-iminobis(N,N-di(i-butyl)propylamine), 3,3'-iminobis(N,N-di(t-butyl)propylamine), 2,9-dimethyl-2,5,9-triazadecane, 2,10-dimethyl-2,10-triazadecane, 2,12-dimethyl-2,6,12-triazatridecane, 2,12-dimethyl-2,5,12-triazatridecane, 2,16-dimethyl-2,9,16-triazaheptadecane, 3-ethyl-10-methyl-3,6,10-triazaundecane, 5,13-di(n-butyl)-5,9,13-triazaheptadecane, di(2-picolyl)amine, and di(3-picolyl)amine. Among others, N,N-dimethylaminopropylamine, N,N-diethylaminopropylamine, and N,N-dibutylaminopropylamine are preferable.

In formula (1), $R_1$ and $R_2$ are preferably each independently a group represented by the following formula (2) or (3).

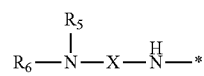

(2)

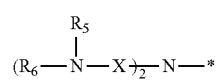

(3)

wherein * shows a position of bonding with a triazine ring; each X independently represents an alkylene group having 1 to 4 carbon atoms; and $R_5$ and $R_6$ each independently represent a hydrogen atom or an alkyl group having 1 to 6 carbon atoms, $R_5$ and $R_6$ optionally bond to each other to form a cyclic structure, and the cyclic structure optionally contains a hetero atom.

In formula (1), the groups represented by $R_3$ and $R_4$ are preferably each independently a hydrogen atom, an alkyl group, or an alkoxy group, and are more preferably each independently a hydrogen atom, an alkyl group having 1 to 3 carbon atoms, or an alkoxy group having 1 to 3 carbon atoms.

The pigment dispersant of the present invention exhibits an excellent action even in a small amount as a dispersant for a pigment. In addition, in a pigment composition and a pigment colorant which are each prepared using the pigment dispersant of the present invention, viscosity increase or gelation during storage is unlikely to occur, so that foreign substances are unlikely to occur in a coating film which is formed using these. Specific examples of the pigment dispersant of the present invention include compounds represented by the following formulas (A) to (F).

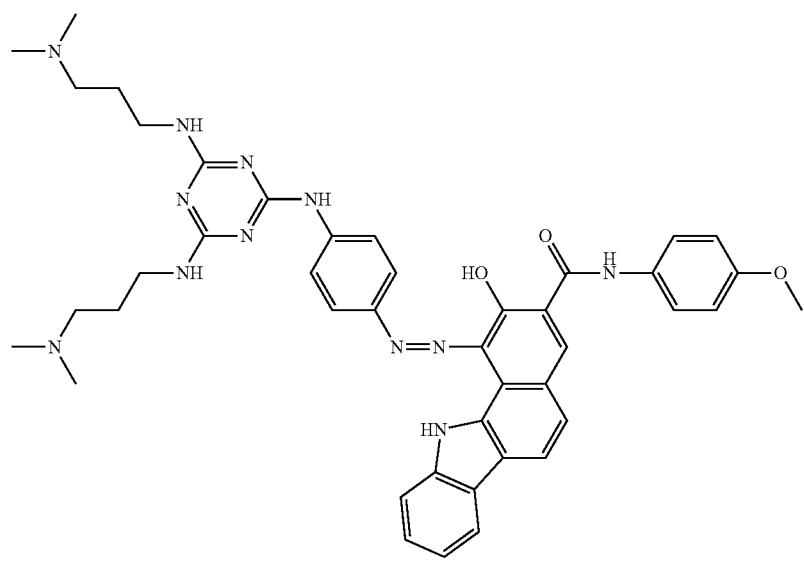
(A)
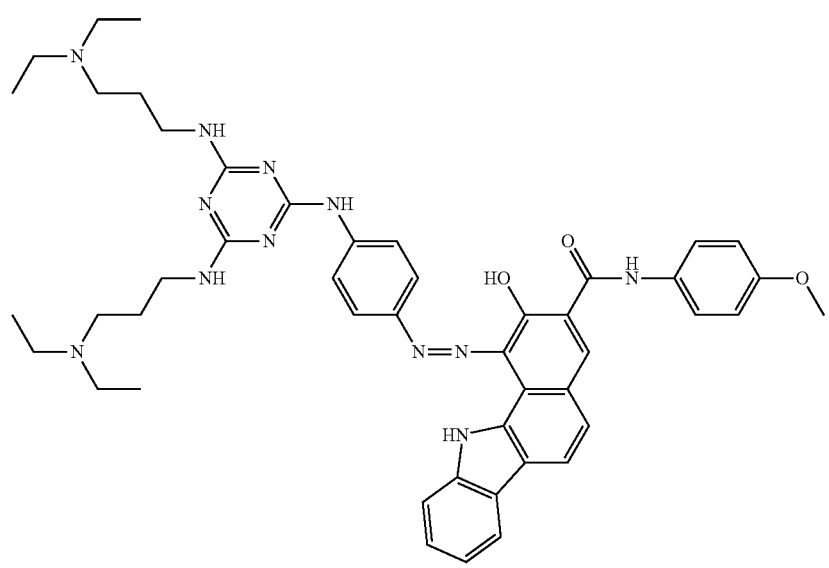
(B)

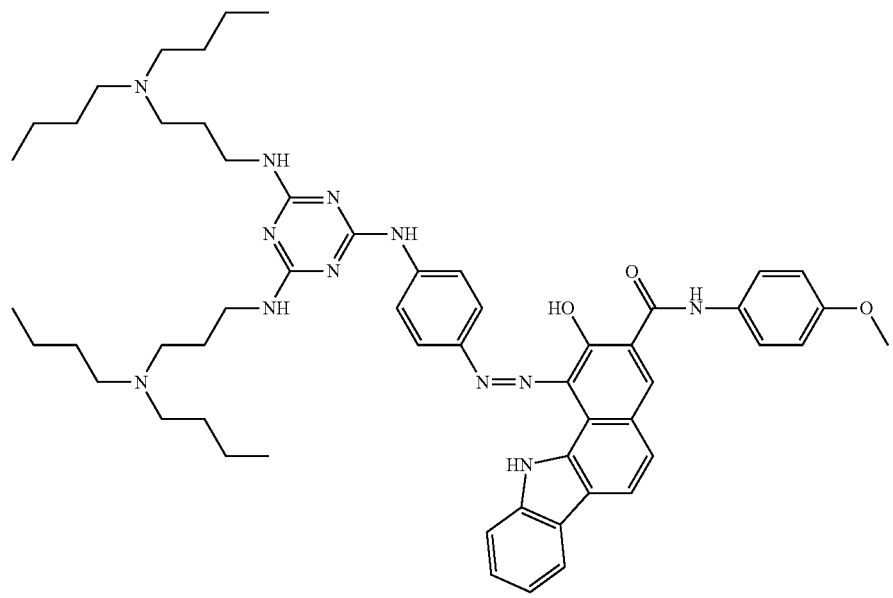
(C)
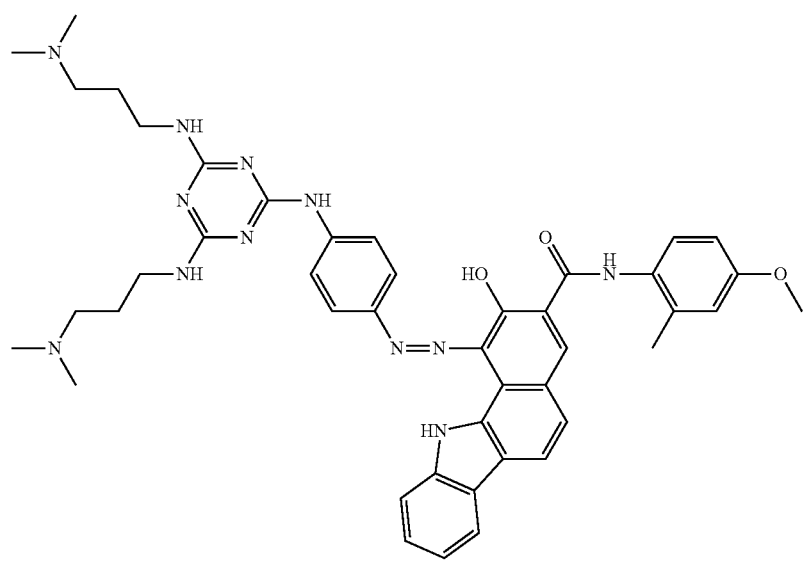
(D)

(E)
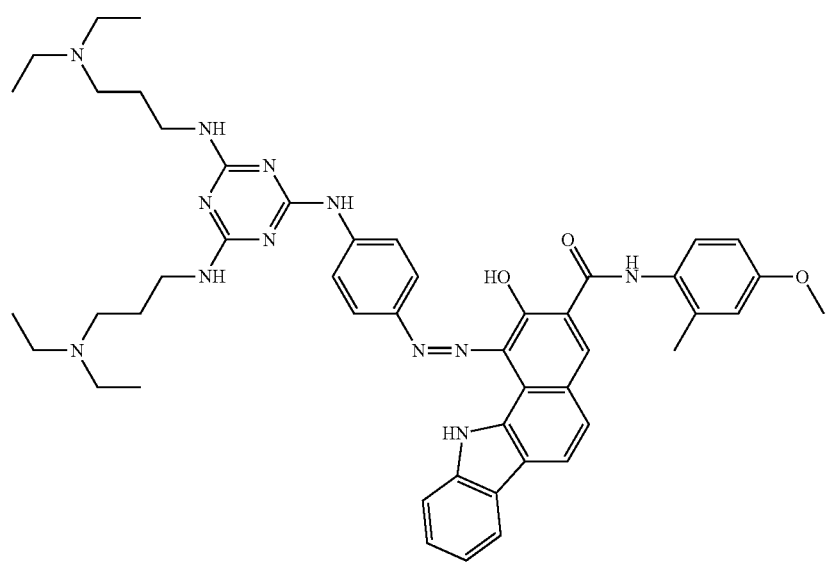
(F)
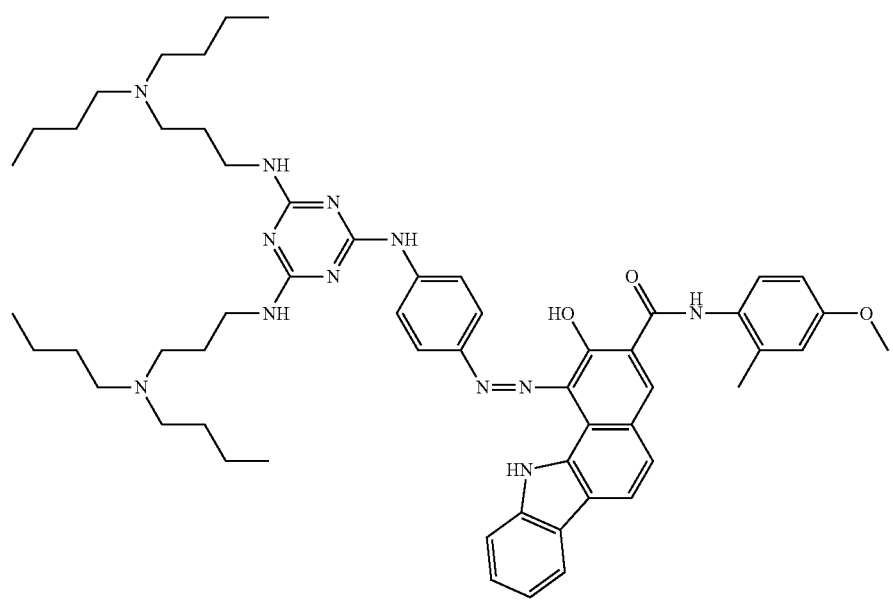
Further specific examples of the pigment dispersant of the present invention include compounds represented by the following formulas (1-1) to (1-8).

(1-1)
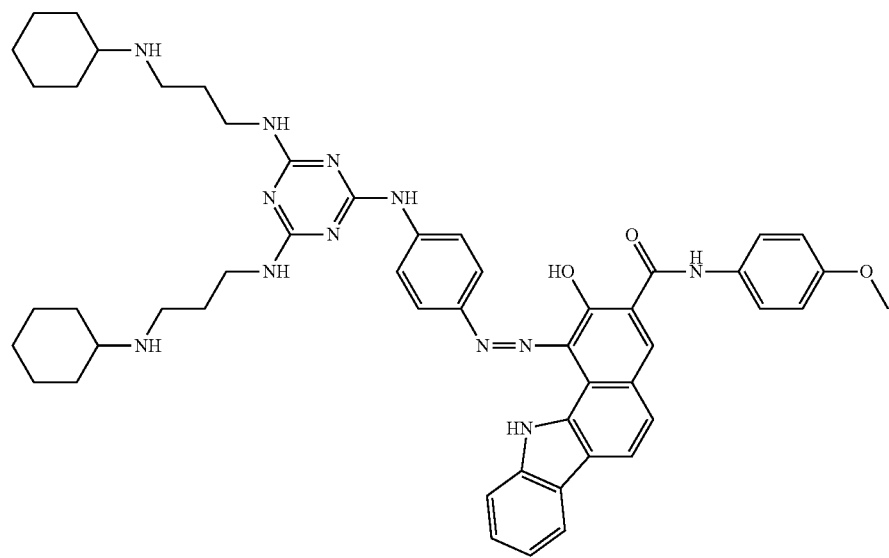
(1-2)
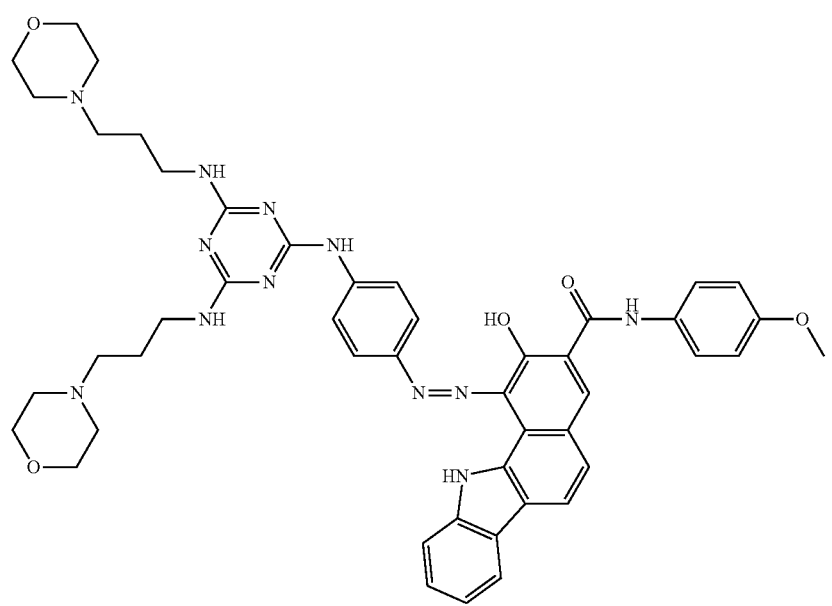

(1-3)
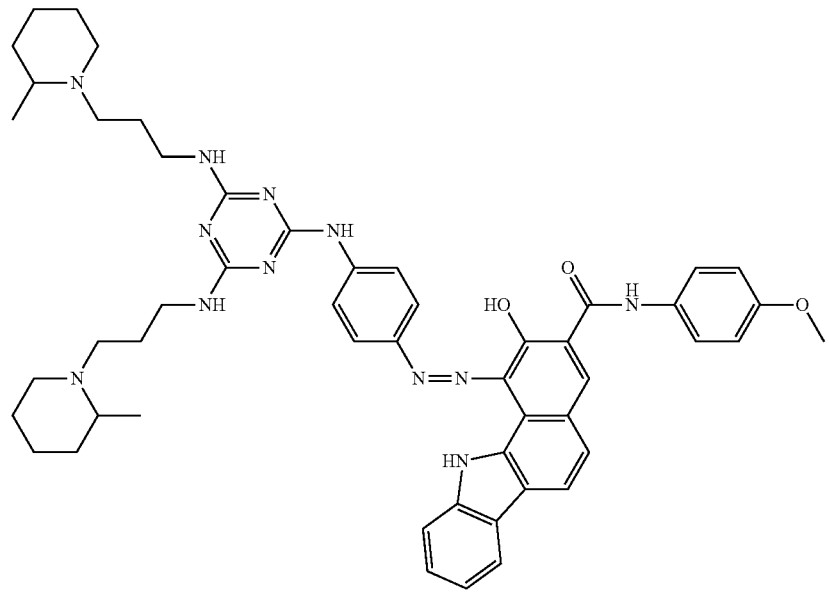
(1-4)
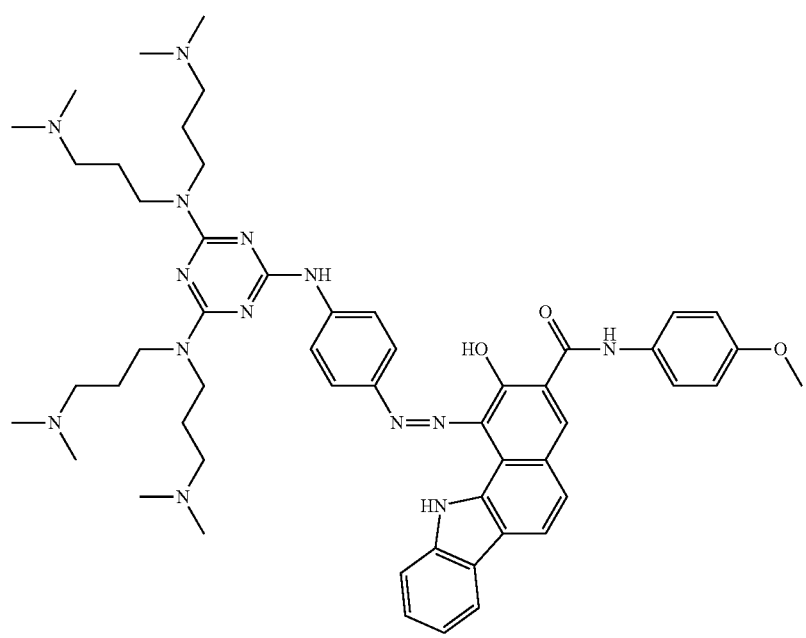

(1-5)
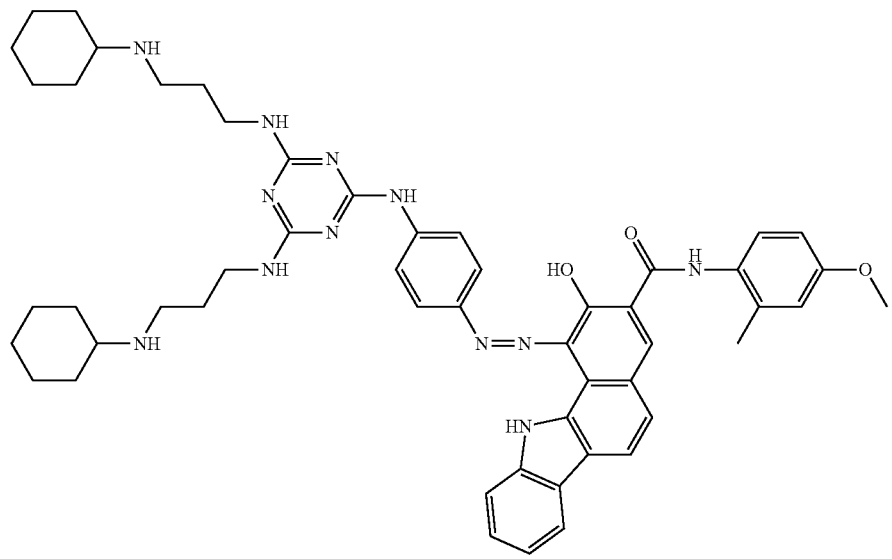
(1-6)
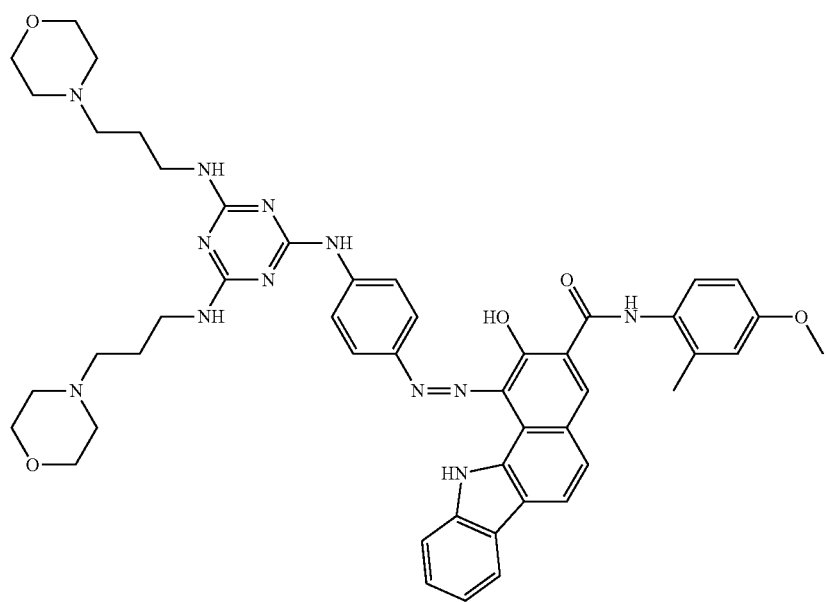

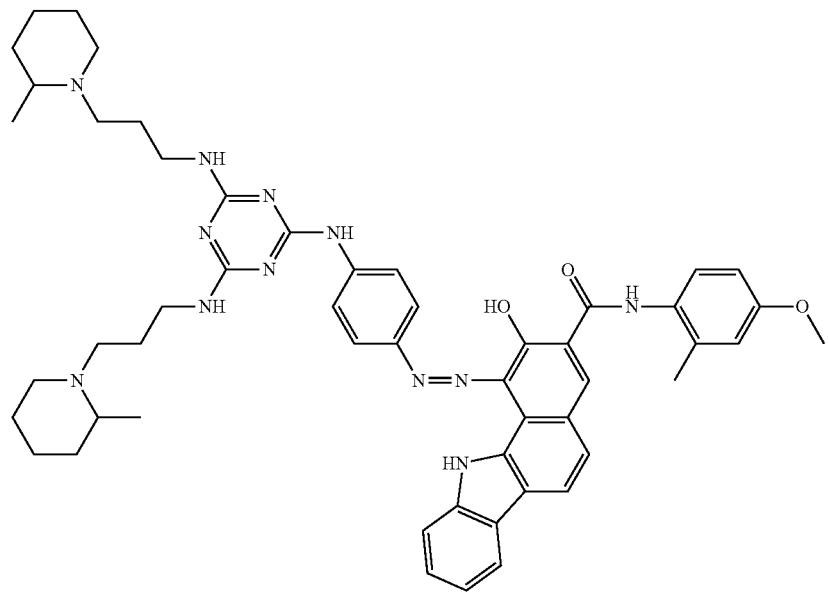

(1-7)

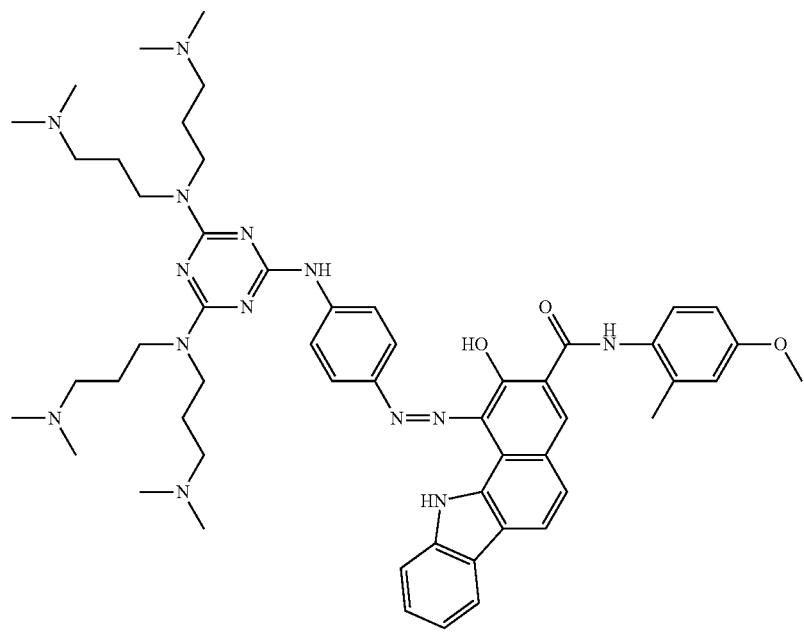

(1-8)

The compound (the first pigment dispersant) represented by formula (1) can be synthesized, for example, in the following manner. Firstly, cyanuric chloride and 4'-aminoacetanilide are reacted in water acidified with acetic acid at 0 to 10° C. Subsequently, a reaction product is reacted with the previously described particular amine compound at 70 to 80° C., and deacetylation is then performed under acidity of hydrochloric acid at 90 to 100° C. Thereafter, a deacetylated product is cooled to 0 to 10° C. and is then subjected to diazotization using sodium nitrite. A diazotized product is subjected to a coupling reaction with a particular coupler, such as N-(4-methoxyphenyl)-2-hydroxy-11H-benzo[a]carbazole-3-carboxamide, and the compound (the first pigment dispersant) represented by formula (1) can thereby be obtained. It is to be noted that there is a possibility that small amounts of unreacted raw materials and by-products are contained in the pigment dispersant of the present invention; however, these unreacted raw materials and by-products may each be contained in a slight amount as long as the effects of the present invention are obtained.

Examples of the particular coupler which are used in the above-described synthesis method include N-phenyl-2-hydroxy-11H-benzo[a]carbazole-3-carboxamide, N-(4-methoxyphenyl)-2-hydroxy-11H-benzo[a]carbazole-3-carboxamide, and N-(2-methyl-4-methoxyphenyl)-2-hydroxy-11H-benzo[a]carbazole-3-carboxamide.

(Second Pigment Dispersant)

One of the main characteristics of a pigment dispersant (the second pigment dispersant) of the present invention is that it is a compound represented by the following formula (4). The pigment dispersant of the present invention having such a characteristic has an excellent affinity to various pigments and can suitably be used as a pigment dispersant for dispersing various pigments irrespective of organic and inorganic pigments. In addition, the pigment dispersant of the present invention has an excellent pigment-dispersing effect and therefore can be used as a material for preparing pigment colorants for various uses.

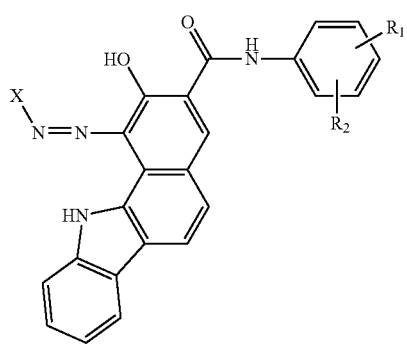

(4)

wherein X represents an aromatic group having at least one sulfonate group, and R₁ and R₂ each independently represent a hydrogen atom, a halogen atom, an alkyl group, an alkoxy group, or a hydroxy group.

The aromatic group represented by X in formula (4) optionally has a substituent other than the sulfonate group. Examples of the substituent other than a sulfonate group include a halogen atom, an alkyl group, an alkoxy group, and a hydroxy group. Examples of the halogen atom include a fluorine atom (F), a chlorine atom (Cl), and a bromine atom (Br).

In formula (4), X is preferably a group represented by any one of the following formulas (5) to (7).

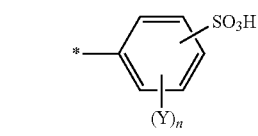

(5)

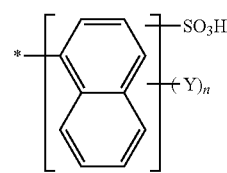

(6)

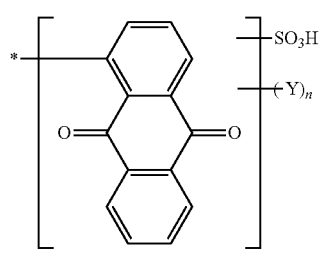

(7)

wherein * shows a position of bonding with a nitrogen atom, each Y independently represents a halogen atom, and n represents a number of 0 to 2.

In formulas (5) to (7), specific examples of the halogen atom represented by Y include a fluorine atom (F), a chlorine atom (Cl), and a bromine atom (Br).

The pigment dispersant of the present invention exhibits an excellent action even in a small amount as a dispersant for a pigment. In addition, in a pigment composition and a pigment colorant which are each prepared using the pigment dispersant of the present invention, viscosity increase or gelation during storage is unlikely to occur, so that foreign substances are unlikely to occur in a coating film which is formed using these. Specific examples of the pigment dispersant of the present invention include compounds represented by the following formulas (H) to (M).

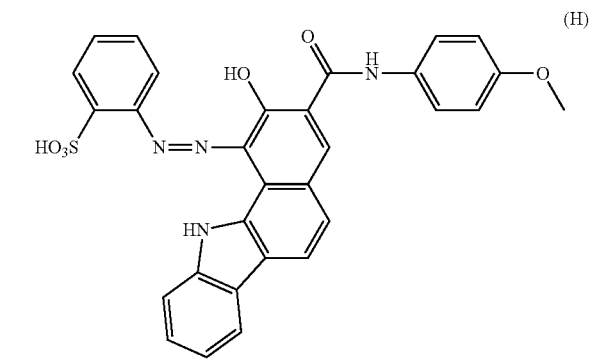

(H)

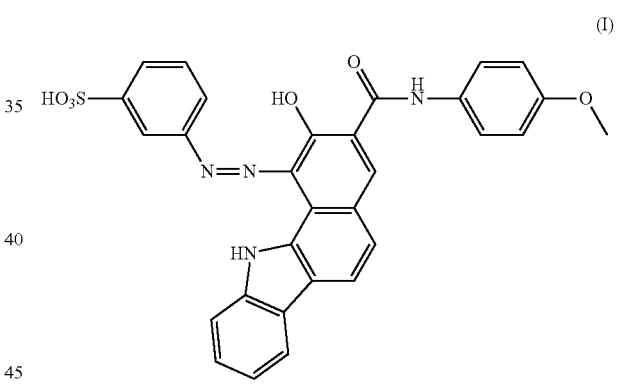

(I)

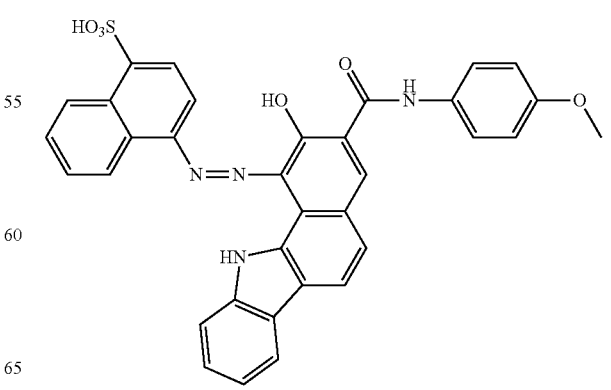

(J)

(K)
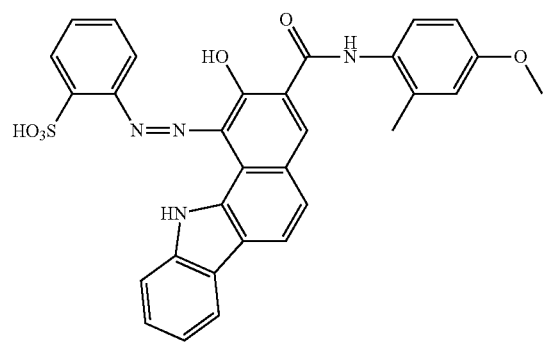
(L)
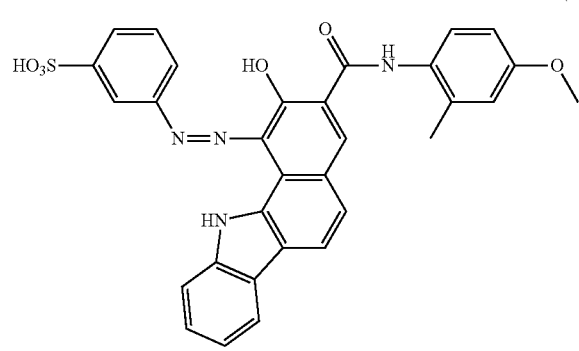
(M)
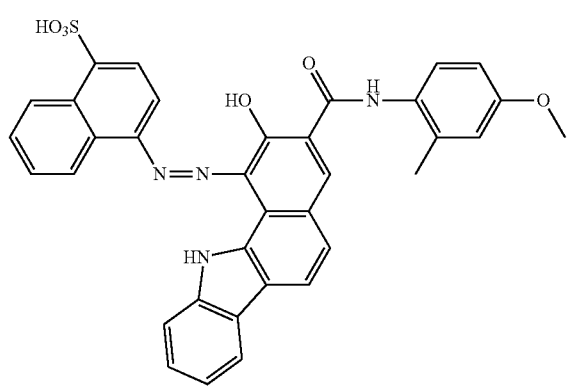
(4-1)
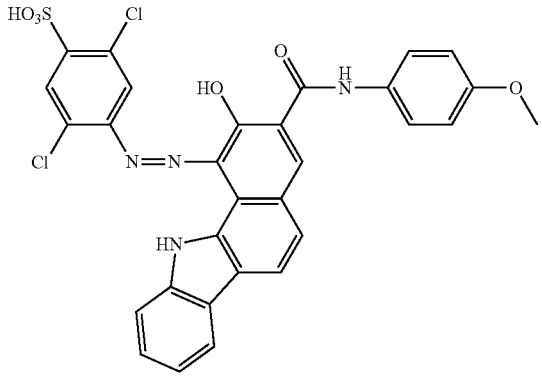
(4-2)
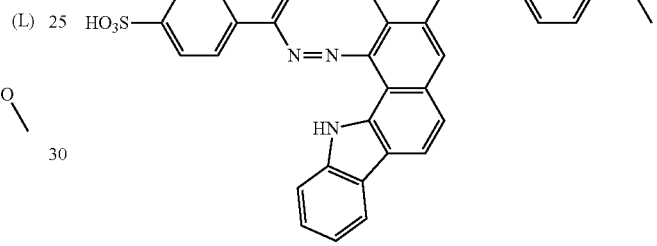
(4-3)
(4-4)
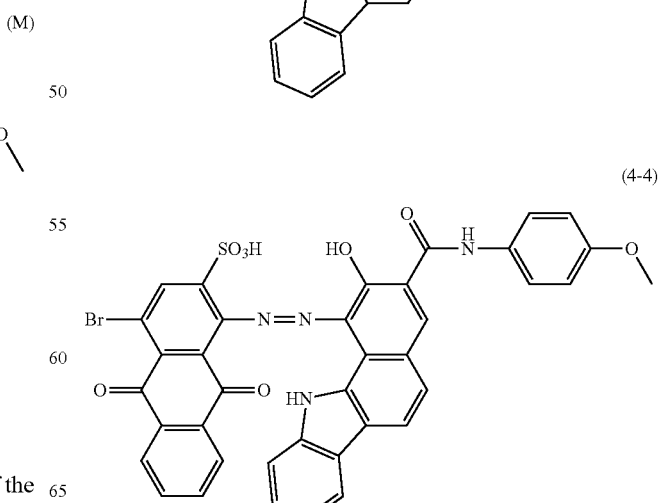
Further specific examples of the pigment dispersant of the present invention include compounds represented by the following formulas (4-1) to (4-8).

(4-5)
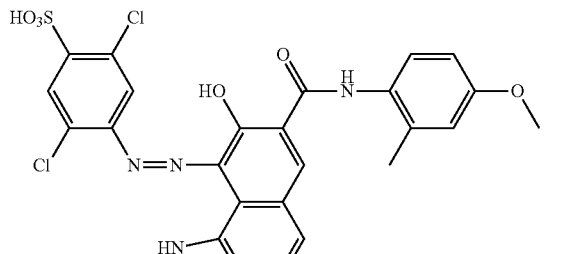

(4-6)
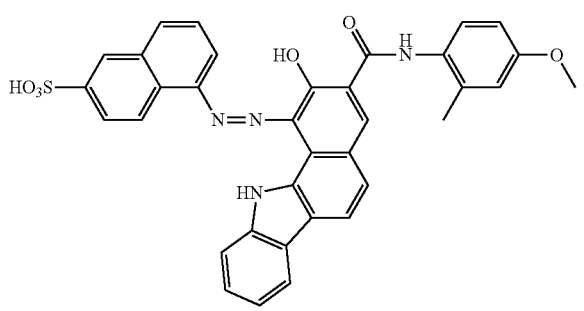

(4-7)
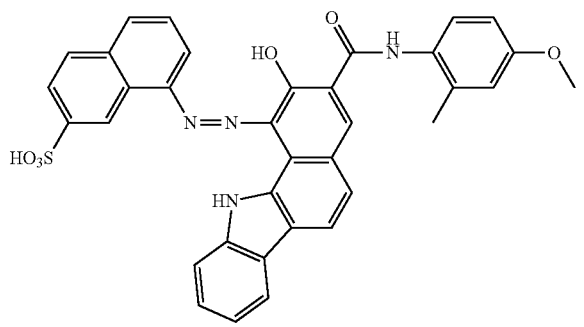

(4-8)
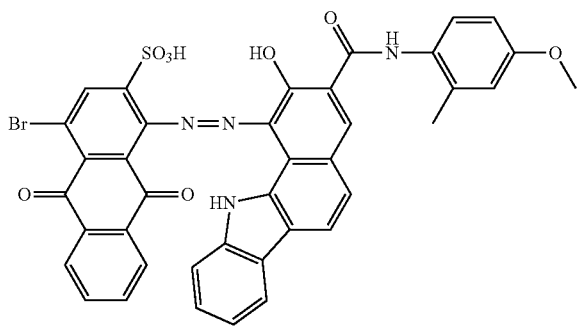

The compound (the second pigment dispersant) represented by formula (4) can be synthesized, for example, in the following manner. Firstly, an aromatic amine having at least one sulfonate group is diazotized by an ordinary method. Subsequently, a diazotized product is subjected to a coupling reaction with a particular coupler, such as N-(4-methoxyphenyl)-2-hydroxy-11H-benzo[a]carbazole-3-carboxamide, and the compound (the second pigment dispersant) represented by formula (4) can thereby be obtained. It is to be noted that there is a possibility that small amounts of unreacted raw materials and by-products are contained in the pigment dispersant of the present invention; however, these unreacted raw materials and by-products may each be contained in a slight amount as long as the effects of the present invention are obtained.

Specific examples of the aromatic amine having at least one sulfonate group, which is used in the above-described synthesis method, include o-aminobenzenesulfonic acid, m-aminobenzenesulfonic acid, p-aminobenzenesulfonic acid, 2-chloroaniline-3-sulfonic acid, 2-chloroaniline-5-sulfonic acid, 4-chloroaniline-2-sulfonic acid, 4-chloroaniline-3-sulfonic acid, 2,5-dichloroaniline-4-sulfonic acid, 4,5-dichloroaniline-2-sulfonic acid, 2-nitroaniline-4-sulfonic acid, o-anisidine-5-sulfonic acid, p-anisidine-5-sulfonic acid, o-toluidine-4-sulfonic acid, m-toluidine-4-sulfonic acid, p-toluidine-2-sulfonic acid, 2-chloro-p-toluidine-3-sulfonic acid, 2-chloro-p-toluidine-5-sulfonic acid, 4-chloro-m-toluidine-2-sulfonic acid, 3-amino-6-chlorotoluene-4-sulfonic acid, 3-amino-6-chloro-4-sulfobenzoic acid, 1-amino-8-naphthalenesulfonic acid, 2-amino-1-naphthalenesulfonic acid, 4-amino-1-naphthalenesulfonic acid, 5-amino-1-naphthalenesulfonic acid, 6-amino-1-naphthalenesulfonic acid, 5-amino-3-naphthalenesulfonic acid, 3-amino-1,5-naphthalenedisulfonic acid, 3-amino-2,7-naphthalenedisulfonic acid, 4-amino-1,5-naphthalenedisulfonic acid, 6-amino-1,3-naphthalenedisulfonic acid, 7-amino-1,3-naphthalenedisulfonic acid, 4-amino-5-hydroxy-2,7-naphthalenedisulfonic acid, 1-amino-2-hydroxy-4-naphthalenesulfonic acid, 6-amino-4-hydroxy-2-naphthalenesulfonic acid, 7-amino-4-hydroxy-2-naphthalenesulfonic acid, 1-amino-2-anthraquinonesulfonic acid, 1-amino-5-anthraquinonesulfonic acid, 1-amino-8-anthraquinonesulfonic acid, and 1-amino-4-bromoanthraquinone-2-sulfonic acid.

Examples of the particular coupler which are used in the above-described synthesis method include N-phenyl-2-hydroxy-11H-benzo[a]carbazole-3-carboxamide, N-(4-methoxyphenyl)-2-hydroxy-11H-benzo[a]carbazole-3-carboxamide, and N-(2-methyl-4-methoxyphenyl)-2-hydroxy-11H-benzo[a]carbozole-3-carboxamide.

(Method of Using Pigment Dispersant)

The method of using the pigment dispersant of the present invention is not particularly limited, and the use methods described below are given as examples. The intended effect of dispersing pigment can be obtained by any of the methods.

(1) Mixing a pigment and the pigment dispersant in advance by a known method, and adding a resultant pigment composition to a vehicle or the like, thereby dispersing the pigment in the vehicle.

(2) Separately adding a pigment and the pigment dispersant in a predetermined ratio to a vehicle or the like, thereby dispersing the pigment in the vehicle.

(3) Separately dispersing a pigment and the pigment dispersant each in a vehicle or the like, and then mixing resultant respective dispersion liquids in a predetermined ratio, thereby dispersing the pigment in the vehicle.

(4) Adding the pigment dispersant in a predetermined ratio to a dispersion liquid obtained by dispersing a pigment in a vehicle or the like, thereby dispersing the pigment in the vehicle.

<Pigment Composition>

A pigment composition of the present invention contains a pigment and the previously described pigment dispersant. The content of the pigment dispersant based on 100 parts by mass of the pigment is preferably 0.5 to 40 parts by mass, and is more preferably 1 to 20 parts by mass. When the content of the pigment dispersant is less than the above-described range, the intended effects of the dispersant are not obtained sufficiently in some cases. On the other hand, when the content of the pigment dispersant is larger than the above-described range, the effects of the dispersant hit the ceiling, and an effect more than that cannot be expected, so that the pigment composition is made disadvantageous in terms of productivity because the costs of materials increase, or by other reasons. Further, in a paint or an ink using such a pigment composition containing the pigment dispersant excessively, various physical properties of a vehicle are deteriorated, or the hue of the pigment remarkably changes due to the color of the pigment dispersant itself in some cases.

Examples of the pigment in which an effective dispersion effect is obtained by using the pigment dispersant of the present invention include anthraquinone-based pigments, quinacridone-based pigments, diketopyrrolopyrrole-based pigments, indigo/thioindigo-based pigments, perinone-based pigments, perylene-based pigments, phthalocyanine-based pigments, indoline-based pigments, isoindoline-based pigments, isoindolinone-based pigments, dioxazine-based pigments, quinophthalone pigments, nickel azo pigments, metal complex pigments, insoluble azo-based pigments, soluble azo-based pigments, high-molecular-weight azo-based pigments, azomethine azo-based black pigments, and aniline black-based pigments. Among others, it is particularly preferable to use the pigment dispersant of the present invention for a pigment the hue of which is black because more remarkable effects are obtained. As such a pigment the hue of which is black, 1-[4-[(4,5,6,7-tetrachloro-3-oxoisoindoline-1-ylidene)amino]phenylazo]-2-hydroxy-N-(4-methoxy-2-methylphenyl)-11H-benzo[a]carbazole-3-carboxamide, which is an azomethine azo-based black pigment (black azo pigment), is preferable.

A method of producing the pigment composition of the present invention is not particularly limited. For example, By mixing a pigment and the pigment dispersant by a conventionally known method, the pigment composition of the present invention can be obtained. It is to be noted that specific examples of the method of producing the pigment composition of the present invention include the methods of (1) to (4) described below.

(1) A method of mixing a powder of a pigment and a powder of the pigment dispersant without using a disperser.
(2) A method of mixing a pigment and the pigment dispersant mechanically with any one of various dispersers, such as a kneader, a roll, an attritor, or a horizontal type bead mill.
(3) A method of adding and mixing a liquid obtained by dissolving or finely dispersing the pigment dispersant therein to a water-based or organic solvent-based suspension of a pigment, thereby depositing the pigment dispersant uniformly on the surface of the pigment.
(4) A method of dissolving a pigment and the pigment dispersant in a solvent, such as sulfuric acid, having strong dissolving power, and then coprecipitating the pigment and the pigment dispersant with a poor solvent, such as water.

The nature of the pigment dispersant which is used for preparing the pigment composition may be any of a solution, a slurry, a paste, and a powder. Even if the pigment dispersant having any of the natures is used, the desired effects can be obtained.

The pigment composition containing: a black azo pigment that has optical properties of transmitting light in an infrared region, especially light in a near infrared region, satisfactorily and almost shielding light in a visible light region; and the previously described pigment dispersant is described herein. This pigment composition can suitably be used, for example, for an infrared filter which is mounted on an electronic device that utilizes infrared rays. In addition, printed texts using this pigment composition transmits near infrared rays without absorbing them, and therefore this pigment composition can suitably be used, for example, also for a PTP (Press-Through-Pack) package ink, in which printed texts on an aluminum packaging material are not obstacles in detecting foreign substances. Further, the above-described black azo pigment, which is different from an electrically conductive material such as carbon black, has excellent electric insulation. Therefore, the pigment composition containing this black azo pigment and the previously described pigment dispersant is also suitable as, for example, a material for forming a black matrix (BM) of a color filter (CF).

<Pigment Colorant>

A pigment colorant of the present invention contains the previously described pigment composition and a film-forming material. The pigment colorant of the present invention can be used in wide fields as a colorant or the like for displaying images, recording images, a gravure printing ink, a writing ink, a plastic, pigment printing, and a paint. Particularly, the pigment colorant of the present invention is suitable as a colorant for a black matrix of a color filter. Further, the pigment colorant of the present invention is particularly useful also as a material for an image recording agent such as a gravure printing ink. By using the pigment colorant of the present invention, a material for an image recording agent that can provide a high-quality image can be prepared.

The amount of the pigment composition in the pigment colorant of the present invention is preferably 5 to 500 parts by mass, and is more preferably 50 to 250 parts by mass based on 100 parts by mass of the film-forming material. The pigment colorant of the present invention can be prepared by, for example, mixing a micronized pigment and a film-forming material, such as a resin ((co)polymer), an oligomer, or a monomer.

In addition, the pigment colorant of the present invention can also be prepared by mixing the pigment composition and a liquid containing the above-described film-forming material. As the liquid containing the film-forming material, a liquid containing a photosensitive film-forming material, a liquid containing a non-photosensitive film-forming material, or the like can be used. Specific examples of the liquid containing a photosensitive film-forming material include a liquid containing a photosensitive film-forming material which is used for an ultraviolet ray-curable ink, an electron beam-curable ink, or the like. In addition, specific examples of the liquid containing a non-photosensitive film-forming material include: varnish which is used for a printing ink, such as a letterpress ink, a planographic ink, a gravure ink, or a screen ink; varnish which is used for an ordinary temperature-drying or baking paint; varnish which is used for electrodeposition coating; and varnish which is used for a thermal transfer ribbon.

Specific examples of the photosensitive film-forming material include photosensitive resins, such as a photosensitive cyclized rubber-based resin, a photosensitive phenol-based resin, a photosensitive polyacrylate-based resin, a photosensitive polyamide resin, a photosensitive polyimide-based resin, an unsaturated polyester-based resin, a polyester acrylate-based resin, a polyepoxy acrylate-based resin, a polyurethane acrylate-based resin, a polyether acrylate-based resin, and a polyol acrylate-based resin. Various monomers may be added as a reactive diluent to the liquids containing these photosensitive resins.

By adding a photopolymerization initiator, such as a benzoin ether or benzophenone, to the pigment colorant containing a photosensitive resin as a film-forming material, and milling a resultant mixture by a conventionally known method, the pigment colorant can be made into a photocurable, photosensitive pigment dispersion liquid. In addition, when a thermal polymerization initiator is used in place of the above-described photopolymerization initiator, the pigment colorant can be made into a thermally curable pigment dispersion liquid.

Specific examples of the non-photosensitive film-forming material include a styrene-(meth)acrylic acid ester-based copolymer, a soluble polyamide-based resin, a soluble polyimide-based resin, a soluble polyamideimide-based resin, a soluble polyester imide-based resin, a water-soluble amino polyester-based resin, water-soluble salts thereof, a water-soluble salt of a styrene-maleic acid ester-based copolymer, and a water-soluble salt of a (meth)acrylic acid ester-(meth) acrylic acid-based copolymer.

The pigment colorant of the present invention can further contain a polymer dispersant. As the polymer dispersant, an acidic polymer dispersant and a basic polymer dispersant can be used. The amount of the polymer dispersant to be compounded is preferably 2 to 100 parts by mass, and is more preferably 10 to 50 parts by mass based on 100 parts by mass of the pigment.

Next, further details on the pigment colorant of the present invention will be described taking a pigment dispersion liquid for a black matrix of a color filter (pigment colorant for BM) as a representative example. To prepare the pigment colorant (photoresist) for BM, the previously described pigment composition containing a black pigment, such as a black azo pigment, is first added to the liquid containing a film-forming material to perform premixing. Subsequently, a dispersion treatment is performed, and thereby the pigment colorant for BM can be prepared. More specifically, by adding the pigment composition ground uniformly using a dispersion machine, such as a vertical type medium disperser, a horizontal type medium disperser, or a ball mill, to the liquid containing a film-forming material, and mixing a resultant mixture, the pigment colorant for BM can be obtained. In addition, a solution obtained by dissolving the black azo pigment and the pigment dispersant in sulfuric acid or the like and water are mixed to precipitate as a solid solution or a co-precipitate the pigment composition containing the black azo pigment and the pigment dispersant, thereby separating the pigment composition. The pigment colorant for BM can also be obtained by adding the separated pigment composition to a liquid containing a film-forming material, a polymer dispersant, and the like and mixing a resultant mixture, and then performing dispersion by grinding using a horizontal type wet medium disperser (bead mill), such as DYNO-MILL.

As the liquid containing a film-forming material, which is used for preparing the pigment colorant for BM, a solution of a film-formable polymer which is contained in a conventionally known pigment dispersion liquid for a color filter can be used. In addition, examples of the liquid medium which is used for the liquid containing a film-forming material include an organic solvent, water, and a mixed liquid of an organic solvent and water. It is to be noted that if necessary, conventionally known additives such as, for example, a dispersion auxiliary agent, a smoothing agent, and an adherence agent, can be added to the pigment colorant for BM.

By using the above-described pigment colorant for BM, which contains a black azo pigment dispersed with the pigment dispersant, a black matrix (BM) for a CF substrate, which is substantially electrically insulating, can be formed. BM can be formed on a CF substrate using the pigment colorant for BM by a method, such as, for example, a photolithography method, a laser abrasion method, an inkjet print method, a printing method, a transfer method, or a sticking method.

The film thickness of BM is, for example, 0.5 to 3 μm, and may usually be 1 to 2 μm. In addition, by using the above-described pigment colorant for BM, BM having a sufficient optical density, can be formed. The optical density of BM to be formed can be made, for example, 1.6 or more, preferably 2.0 or more. Specific methods in the case where BM is allowed to have a function as a spacer include: a method of forming BM itself in such a way as to be thick; a method of stacking a pixel on BM; a method of stacking a colorless resin film on BM; and so on. In any of the methods, the film thickness is preferably set in such a way as to be about 5 to about 10 μm. Thereafter, by using a known colorant for forming a chromatic color pixel, a chromatic color pixel can further be formed on the CF substrate on which BM has been formed.

EXAMPLES

Next, the present invention will be described more specifically giving Examples and Comparative Examples. Hereinafter, "part(s)" and "%" are each on a mass basis unless otherwise noted.

Preparation (1) of Pigment Dispersants

Example 1-1

To 100 parts of water, 14.8 parts of cyanuric chloride, 12 parts of 4'-aminoacetanilide, and 9.6 parts of acetic acid were added and reacted at 0 to 10° C. for 1 hour. After 24.5 parts of N,N-dimethylaminopropylamine was added, and a resultant mixture was reacted at 70 to 80° C. for 2 hours, 33 parts of concentrated hydrochloric acid was further added. After a resultant mixture was reacted at 90 to 100° C. for 1 hour to perform deacetylation, a reaction mixture was cooled to 0 to 10° C., and 6 parts by sodium nitrite was added to perform diazotization, thereby obtaining a solution of a diazonium salt. On the other hand, a solution was prepared by dissolving 30.5 parts of N-(4-methoxyphenyl)-2-hydroxy-11H-benzo[a]carbazole-3-carboxamide and 26 parts of sodium hydroxide in 800 parts of methanol. The solution of the diazonium salt was added to the prepared solution to perform a coupling reaction at 20 to 30° C. for 5 hours. After filtration and washing with water were performed, drying was performed to obtain 49 parts of a blue-violet pigment dispersant (A) represented by the following formula (A).

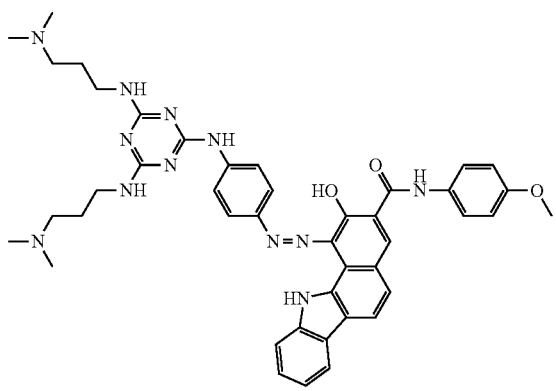

(A)

A peak of a molecular weight of 780.94 was detected by mass analysis using MALDI (Matrix Assisted Laser Desorption/Ionization). In addition, the purity measured using high-performance liquid chromatography (MODEL 860-CO (manufactured by JASCO Corporation), column: YMC Pack Pro C18 (manufactured by YMC CO., LTD.)) was 91%. It was ascertained from the raw materials used, the result of mass analysis, and the result of high-performance liquid chromatography that a compound having an intended structure was obtained.

Example 1-2

A blue-violet pigment dispersant (B) represented by the following formula (B) in an amount of 53 parts was obtained in the same manner as in Example 1-1 described previously, except that 31 parts of N,N-diethylaminopropylamine was used in place of 24.5 parts of N,N-dimethylaminopropylamine.

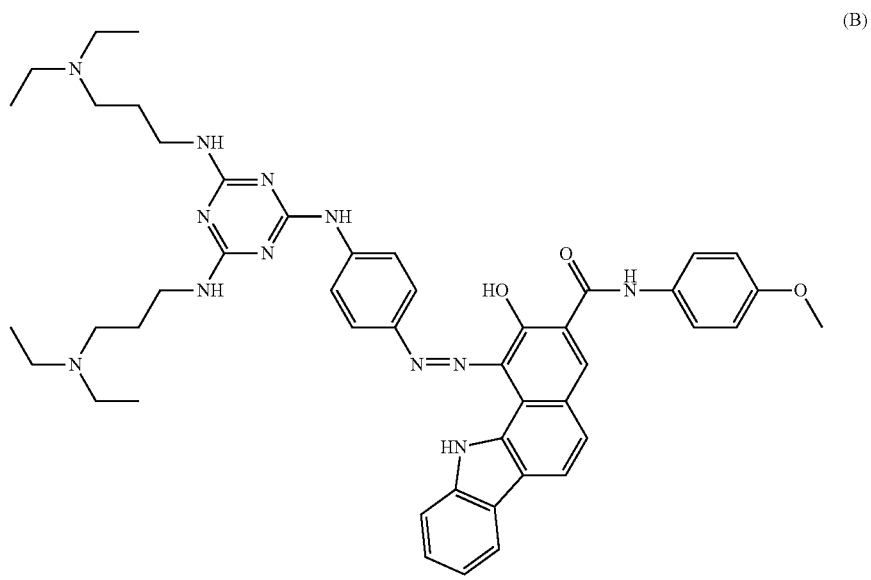 [SMILES: CCN(CC)CCCNc1nc(NCCCN(CC)CC)nc(Nc2ccc(N=Nc3c(O)c(C(=O)Nc4ccc(OC)cc4)cc4ccc5c6ccccc6[nH]c5c34)cc2)n1]

(B)

A peak of a molecular weight of 837.05 was detected by mass analysis using MALDI. In addition, the purity measured using high-performance liquid chromatography was 91%. It was ascertained from the raw materials used, the result of mass analysis, and the result of high-performance liquid chromatography that a compound having an intended structure was obtained.

Example 1-3

A blue-violet pigment dispersant (C) represented by the following formula (C) in an amount of 61 parts was obtained in the same manner as in Example 1-1 described previously, except that 45 parts of N,N-dibutylaminopropylamine was used in place of 24.5 parts of N,N-dimethylaminopropylamine.

(C)

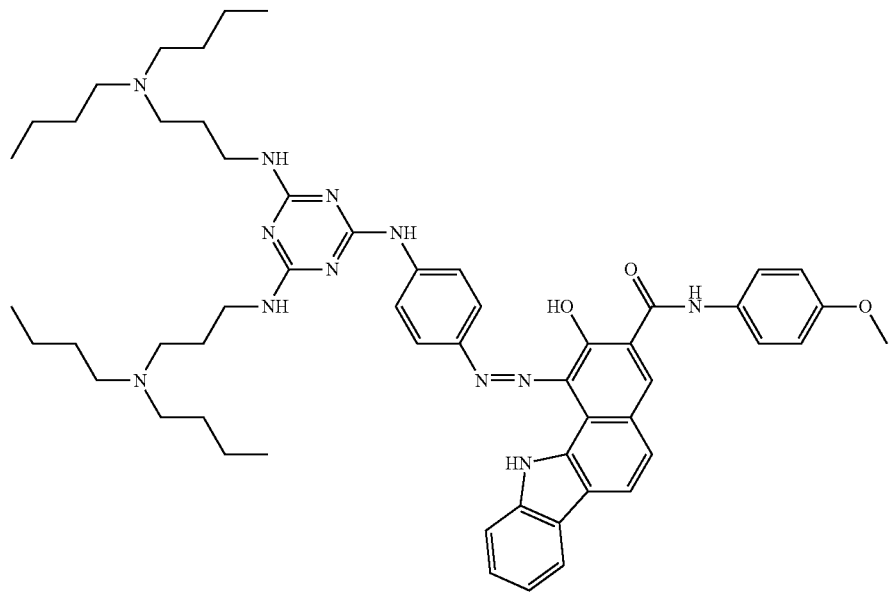

A peak of a molecular weight of 949.27 was detected by mass analysis using MALDI. In addition, the purity measured using high-performance liquid chromatography was 92%. It was ascertained from the raw materials used, the result of mass analysis, and the result of high-performance liquid chromatography that a compound having an intended structure was obtained.

Example 1-4

A blue-violet pigment dispersant (D) represented by the following formula (D) in an amount of 51 parts was obtained in the same manner as in Example 1-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide.

(D)

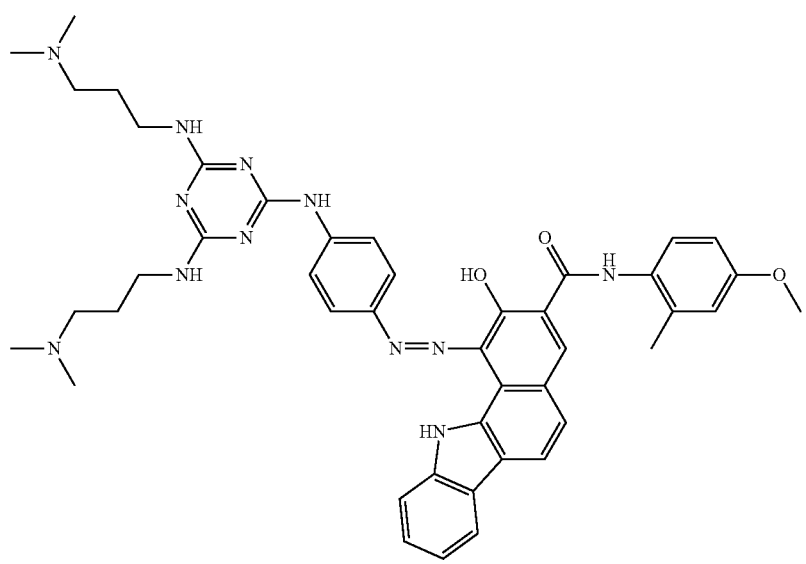

A peak of a molecular weight of 794.97 was detected by mass analysis using MALDI. In addition, the purity measured using high-performance liquid chromatography was 93%. It was ascertained from the raw materials used, the result of mass analysis, and the result of high-performance liquid chromatography that a compound having an intended structure was obtained.

Example 1-5

A blue-violet pigment dispersant (E) represented by the following formula (E) in an amount of 55 parts was obtained in the same manner as in Example 1-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide, and 31 parts of N,N-diethylaminopropylamine was used in place of 24.5 parts of N,N-dimethylaminopropylamine.

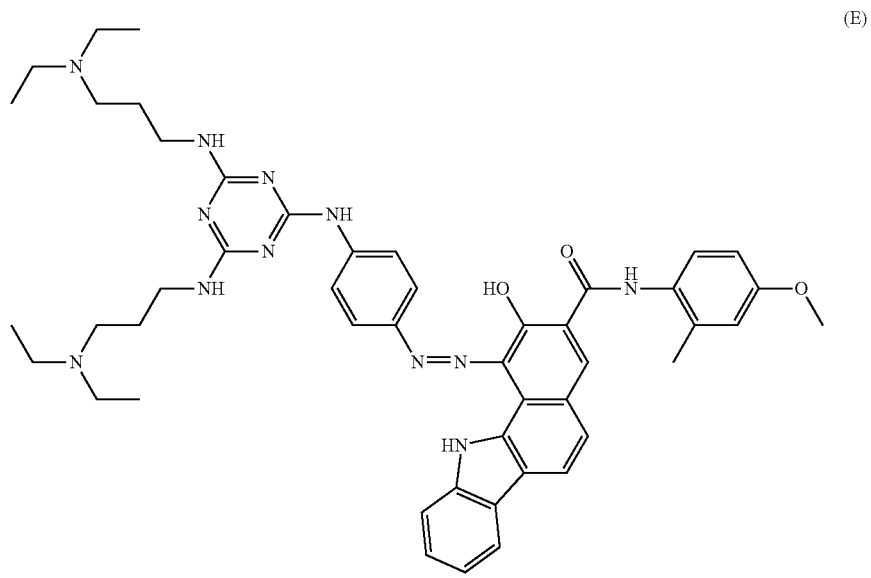 [SMILES: CCN(CC)CCCNc1nc(NCCCN(CC)CC)nc(Nc2ccc(N=Nc3c(O)c(C(=O)Nc4ccc(OC)cc4C)cc4ccc5c6ccccc6[nH]c5c34)cc2)n1]

(E)

A peak of a molecular weight of 851.08 was detected by mass analysis using MALDI. In addition, the purity measured using high-performance liquid chromatography was 94%. It was ascertained from the raw materials used, the result of mass analysis, and the result of high-performance liquid chromatography that a compound having an intended structure was obtained.

Example 1-6

A blue-violet pigment dispersant (F) represented by the following formula (F) in an amount of 62 parts was obtained in the same manner as in Example 1-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide, and 45 parts of N,N-dibutylaminopropylamine was used in place of 24.5 parts of N,N-dimethylaminopropylamine.

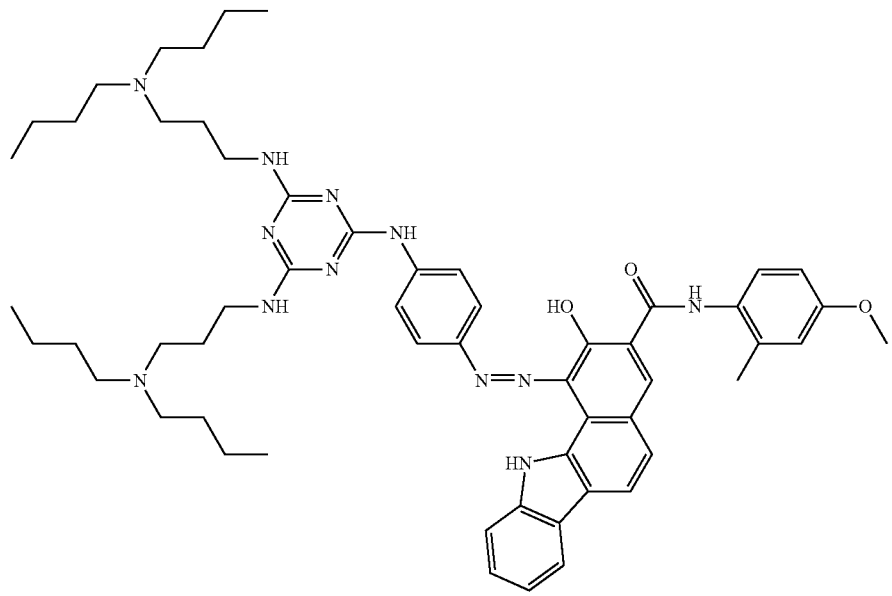

(F)

A peak of a molecular weight of 963.29 was detected by mass analysis using MALDI. In addition, the purity measured using high-performance liquid chromatography was 93%. It was ascertained from the raw materials used, the result of mass analysis, and the result of high-performance liquid chromatography that a compound having an intended structure was obtained.

Preparation (1) of Black Pigment Dispersion Liquids

Example 1-7

[Preparation of Micronized Powder of Black Pigment]

In a kneader to which a pressurization lid is installed, 100 parts of a black pigment (black azo pigment, trade name "CHROMOFINE BLACK A 1103", manufactured by Dainichiseika Color & Chemicals MFG. Co., Ltd.), 500 parts of a sodium chloride powder, and 50 parts of diethylene glycol were loaded. After preliminary mixing was performed until a uniformly wet lump was produced, the pressurization lid was closed, and the contents were kneaded and ground for 2 hours while pressurizing at a pressure of 6 kg/cm$^2$ and controlling the temperature in such a way as to be 92 to 98° C. After a ground product obtained was put into 3,000 parts of water warmed to 80° C., and a resultant mixture was stirred for 1 hour, filtration and washing with water were performed to remove sodium chloride and diethylene glycol, thereby obtaining a press cake. After a nonionic surfactant (in an amount of 200% to the pigment) was added to the obtained press cake, and a resultant mixture was diluted with water, an ultrasonic dispersion treatment was performed to prepare a pigment dispersion liquid. The average particle diameter of fine particles in the pigment dispersion liquid, as measured using a particle size distribution measurement device (trade name "Model N-4", manufactured by Beckman Coulter, Inc.), was about 90 nm. The press cake was dried and pulverized to obtain a micronized powder of the black pigment.

[Preparation of Black Pigment Dispersion Liquids]

Mixing was performed on 25 parts of the micronized powder of the black pigment, 1.5 parts of the pigment dispersant (A) obtained in Example 1-1, 10 parts of a benzyl methacrylate/methacrylic acid/2-hydroxyethyl methacrylate copolymer (molar ratio: 60/20/20, weight average molecular weight of 30,000), 5 parts of an acidic polymer pigment dispersant (trade name "DISPER BYK-110", manufactured by BYK-Chemie GmbH, solid content of 52%), and 65 parts of propylene glycol-1-monomethyl ether-2-acetate. A resultant mixture was premixed and was then subjected to a dispersion treatment using a horizontal type bead mill to obtain a black pigment dispersion liquid (Example 1-7).

Examples 1-8 to 1-12

Black pigment dispersion liquids (Examples 1-8 to 1-12) were each obtained in the same manner as in Example 1-7 described previously, except that the pigment dispersants (B) to (F) were each used in place of the pigment dispersant (A).

Comparative Example 1-1

A black pigment dispersion liquid (Comparative Example 1-1) was obtained in the same manner as in Example 1-7 described previously, except that the pigment dispersant (A) was not used.

Comparative Example 1-2

A black pigment dispersion liquid (Comparative Example 1-2) was obtained in the same manner as in Example 1-7 described previously, except that di(4-methyl-piperidino-1-sulfonyl) copper phthalocyanine (Pigment dispersant (G)) described in Patent Literature 7 was used in place of the pigment dispersant (A).

<Evaluation (1)>

(1) Fluidity (storage stability), (2) gloss of colored surface, and (3) foreign substances in coating film were evaluated for each of the obtained black pigment dispersion liquids. Evaluation methods are described below. In addition, evaluation results are shown in Table 1.

(1) Fluidity (Storage Stability)

The viscosities (mPa·s) of the black pigment dispersion liquids were measured immediately after preparation (initial) and after leaving the black pigment dispersion liquids to stand at 25° C. for 1 month (after leaving black pigments to stand) using an E type viscometer. The measurement conditions were such that the temperature: room temperature (25° C.) and the number of revolutions of the rotor: 6 rpm. "Viscosity after leaving pigment dispersion liquid to stand/initial viscosity (%)" was calculated, and the "storage stability" was evaluated according to the evaluation criteria described below.

Good: "Viscosity after leaving pigment dispersion liquid to stand/initial viscosity" is 110% or less Poor: "Viscosity after leaving pigment dispersion liquid to stand/initial viscosity" exceeds 110%

(2) Gloss of Colored Surface

The black pigment dispersion liquids were each applied on a polypropylene film using a bar coater (thickness of winding wire of 0.45 mm) to form a colored surface. The gloss of the colored surface formed was observed visually and was also observed using a gloss meter to evaluate the "gloss of colored surface" according to the evaluation criteria described below. It is to be noted that the higher the gloss of a colored surface, the more satisfactory the gloss of the colored surface can be determined.

Excellent: very satisfactory
Good: satisfactory
Poor: not satisfactory (3) Foreign Substances in Coating Film The black pigment dispersion liquids were each applied on a glass substrate using a spinner. Drying was performed at 90° C. for 2 minutes, and heating was then performed at 230° C. for 30 minutes to obtain coating films. The surfaces (applied surfaces) of the formed coating films were observed using a microscope (200 magnifications) to check whether foreign substances existed or not, and the "foreign substances in coating film" was evaluated according to the evaluation criteria described below.

Excellent: foreign substances do not exist
Good: slight amounts of foreign substances exist
Poor: foreign substances exist Formation and Evaluation (1) of BM Pattern of CF Example 1-13

(1) Preparation of Photosensitive Black Resist Ink>

Compounded were 40 parts of the black pigment dispersion liquid obtained in Example 1-7, 5 parts of a propylene glycol-1-monomethyl ether-2-acetate solution containing 60% of an acrylated acrylic polyol photosensitive resin, 2 parts of trimethylolpropane triacrylate, 3 parts of dipentaerythritol hexaacrylate, 1 part of a photopolymerization initiator (ethanone-1-[9-ethyl-6-(2-methylbenzoyl)-9H-carbazole-3-yl]-1-(O-acetyl oxime), trade name "Irgacure OXE02", manufactured by BASF SE), and 51 parts of propylene glycol-1-monomethyl ether-2-acetate. After a resultant mixture was stirred sufficiently in such a way as to be uniform using a high-speed stirrer, filtration was performed with a filter having a pore diameter of 3 μm to prepare a photosensitive black resist ink.

(2) Evaluation of Black Coating Film (Resist Film)

The photosensitive black resist ink was applied on a glass substrate using a spin coater. After preliminary drying was performed at 60° C., pre-baking was performed. After exposure was performed in a light quantity of 400 mJ/cm using an ultrahigh pressure mercury lamp, post-baking was performed at 230° C. for 30 minutes to form a black coating film having a thickness of 2 μm. The light transmittance of the formed black coating film from the longer wavelength side of a visible light region to around 670 nm was 20% or less, the light transmittance at 780 nm reached 82%, and the light transmittance increases gradually from 780 nm to reach an equilibrium state. The light transmittance from around 580 to around 625 nm in particular was extremely low, as low as 5% or less. In addition, the volume resistivity of the formed black coating film was $10^{14}$ Ω·cm or more, so that the formed coating film was found to be a high insulation coating film.

(3) Formation of BM Pattern

After the photosensitive black resist ink was applied on a glass substrate using a spin coater, pre-baking was performed at 80° C. for 10 minutes to form a black coating film having a thickness of 2 μm. Exposure was performed through a negative photomask pattern of a BM pattern in a light quantity of 100 mJ/cm using an ultrahigh pressure

TABLE 1

Main compositions and evaluation results of black pigment dispersion liquids

| Black pigment dispersion liquid | Pigment dispersant | Viscosity (mPa·s) Initial | Viscosity (mPa·s) After leaving black pigment dispersion liquid to stand | Viscosity after leaving black pigment dispersion liquid to stand/initial viscosity (%) | Storage stability | Gloss of colored surface | Foreign substances in coating film |
|---|---|---|---|---|---|---|---|
| Comparative Example 1-1 | — | 163 | Gelation | — | Poor | Poor | Poor |
| Comparative Example 1-2 | G | 24 | 31 | 129 | Poor | Good | Good |
| Example 1-7 | A | 13 | 14 | 108 | Good | Excellent | Excellent |
| Example 1-8 | B | 14 | 15 | 107 | Good | Excellent | Excellent |
| Example 1-9 | C | 12 | 13 | 108 | Good | Excellent | Excellent |
| Example 1-10 | D | 12 | 13 | 108 | Good | Excellent | Excellent |
| Example 1-11 | E | 14 | 15 | 107 | Good | Excellent | Excellent |
| Example 1-12 | F | 13 | 14 | 108 | Good | Excellent | Excellent | mercury lamp. After development was performed with an alkaline developing solution, washing with water and drying were performed to form a BM pattern (BM film). The formed BM film is a high insulation coating film and therefore can be used, for example, as a BM film that keeps the thickness of a liquid crystal layer in place of a spacer and can construct a liquid crystal of the IPS type, the COA type, or the like. In addition, the formed BM film sufficiently absorbs visible light up to a longer wavelength region and therefore can suitably be used as BM of a LCD panel that adopts a LED back light.

(4) Preparation of Red, Green, Blue, Yellow, and Violet Pigment Dispersion Liquids Each color pigment dispersion liquid was prepared in the same manner as in Example 1-7 described previously, except that each of PR 254 (diketopyrrolopyrrole red pigment), PR 177 (anthraquinone-based red pigment), PG 36 (copper phthalocyanine green pigment), PB 15:6 (e type copper phthalocyanine blue pigment), PY 185 (yellow pigment), and PV 23 (dioxazine violet pigment) was used in place of CHROMOFINE BLACK A 1103, and a known pigment derivative having a sulfonate group was used.

(5) Preparation of Each Color Photosensitive Resist Ink

A compounded product was obtained by compounding the pigment dispersion liquid in which PR 254 was used and the pigment dispersion liquid in which PR 177 was used in a ratio of 8:2. A photosensitive red resist ink was prepared in the same manner as in the case of the photosensitive black resist ink described previously, except that the compounded product obtained was used in place of the black pigment dispersion liquid.

In addition, a compounded product was obtained by compounding the pigment dispersion liquid in which PG 36 was used and the pigment dispersion liquid in which PY 185 was used in a ratio of 6:4. A photosensitive green resist ink was prepared in the same manner as in the case of the photosensitive black resist ink described previously, except that the compounded product obtained was used in place of the black pigment dispersion liquid.

Further, a compounded product was obtained by compounding the pigment dispersion liquid in which PB 15:6 was used and the pigment dispersion liquid in which PV 23 was used in a ratio of 8:2. A photosensitive blue resist ink was prepared in the same manner as in the case of the photosensitive black resist ink described previously, except that the compounded product obtained was used in place of the black pigment dispersion liquid.

(6) Formation of RGB Pixels of CF

The glass substrate having BM formed thereon was set in a spin coater. After the glass substrate was spin-coated with the prepared photosensitive red resist ink, pre-baking was performed at 80° C. for 10 minutes. Exposure was performed through a photomask having a mosaic pattern in a light quantity of 100 mJ/cm² using a proximity exposure machine equipped with an ultrahigh pressure mercury lamp. After development and washing were performed using a dedicated developing solution and a dedicated rinse, drying was performed to form a mosaic red pattern on the glass substrate. A mosaic green pattern and a mosaic blue pattern were formed in the same manner as described above, except that the photosensitive green resist ink and the photosensitive blue resist ink were used respectively in place of the photosensitive red resist ink. Thereby, CF having BM and RGB pixels each formed thereon was obtained. The obtained CF was such that it exhibits excellent CF properties.

Preparation and Evaluation (1) of Gravure Printing Ink

Example 1-14

Mixing was performed on 10.5 parts of the micronized powder of the black pigment obtained in Example 1-7, 0.5 parts of the pigment dispersant (A) obtained in Example 1-1, and 30 parts of a methyl ethyl ketone:toluene (1:3) mixed solvent solution containing 40% of a polyurethane resin obtained by chain-extending a polyester having an isocyanate at an end thereof with a diamine. After 2 parts of a cationic polymer dispersant, 2.5 parts of a toluene solution containing 40% of a polycarbodiimide compound obtained using tolylene diisocyanate, and 54.5 parts of a methyl ethyl ketone:toluene:isopropyl alcohol (50:30:20) mixed solvent were added, a resultant mixture was mixed sufficiently using a high-speed stirrer. The pigment was dispersed using a horizontal type continuous medium disperser, which uses a glass bead as a dispersion medium, to prepare a black gravure printing ink. Black films were obtained by applying the prepared gravure ink on a polyamide film, a polyester film, and a polypropylene film using a gravure printing machine, thereby perform printing. All the obtained black films were such that they can shield visible light and sufficiently transmit near infrared rays.

Production and Evaluation (1) of Polycarbonate Resin-shaped Plate

Example 1-15

Mixing was performed sufficiently on 20 parts of the micronized powder of the black pigment obtained in Example 1-7, 1 part of the pigment dispersant (A) obtained in Example 1-1, and 80 parts of a polycarbonate resin powder using a Henschel mixer. Subsequently, a resultant mixture was mixed and kneaded using a twin-screw extruder to obtain a master batch containing 20% of the black pigment. After 2 parts of the obtained master batch and 100 parts of polycarbonate resin pellets were mixed using a Henschel mixer, a resultant mixture was kneaded using a twin-screw extruder to obtain black resin pellets. The obtained resin pellets were shaped using an in-line screw injection shaping machine to obtain a black polycarbonate resin-shaped plate (black plate) which is excellent in pigment dispersibility. The obtained black plate was such that it shields visible light and sufficiently transmits near infrared rays, and therefore can be used for uses such as an infrared ray transmission filter.

Production and Evaluation (1) of Acrylic Resin-shaped Plate

Example 1-16

Mixing was performed sufficiently on 20 parts of the micronized powder of the black pigment obtained in Example 1-7, 1 part of the pigment dispersant (A) obtained in Example 1-1, and 80 parts of an acrylic resin (polymethyl methacrylate) powder using a Henschel mixer. Subsequently, a resultant mixture was mixed and kneaded using a twin-screw extrusion kneader to obtain a master batch containing 20% of the black pigment. After 2 parts of the obtained master batch and 100 parts of acrylic resin pellets were mixed using a Henschel mixer, a resultant mixture was kneaded using an extruder to obtain black resin pellets. The obtained resin pellets were shaped using an in-line screw injection shaping machine to obtain a black acrylic resin-shaped plate (black plate) which is excellent in pigment dispersibility. The obtained black plate was such that it shields visible light and sufficiently transmits near infrared rays, and therefore can be used for uses such as an infrared ray transmission filter.

Preparation and Evaluation (1) of Polyurethane Coating Agent

Example 1-17

(1) Preparation of Polyurethane Coating Agent (Liquid)

Kneading was performed sufficiently on 40 parts of the micronized powder of the black pigment obtained in Example 1-7, 2 parts of the pigment dispersant (A) obtained in Example 1-1, and 60 parts of an adipic acid ester-based plasticizer using a three-roll kneader to obtain a plasticizer-dispersed paste of the black pigment (black pigment toner). In addition, 60 parts of a titanium oxide white pigment and 40 parts of an adipic acid ester-based plasticizer were kneaded sufficiently using a three-roll kneader to obtain a plasticizer-dispersed paste of the white pigment (white pigment toner). On the other hand, 100 parts of a methyl ethyl ketone dispersion liquid (solid content: 30%) of a polyether polyol/diphenylmethane diisocyanate-based polyurethane having a carboxy group, 5 parts of a methyl ethyl ketone solution (solid content: 50%) of a polyether polyol/diphenylmethane diisocyanate-based polyurethane, and 2.5 parts of a polycarbodiimide-based crosslinking agent (solid content: 20%) were mixed sufficiently to obtain a mixture. After 1 part of the black pigment toner and 6 parts of the white pigment toner were added to the obtained mixture, a resultant mixture was mixed sufficiently to prepare a gray polyurethane coating liquid.

In addition, a white polyurethane coating liquid was prepared in the same manner as described above, except that the black pigment toner was not used and only the white pigment toner was used. Further, a black polyurethane coating liquid was prepared in the same manner as described above, except that the white pigment toner was not used and only the black pigment toner was used.

(2) Evaluation

After the prepared gray polyurethane coating liquid was applied on the surface of tent cloth of a nylon woven fabric in such a way as to be about 200 g/m$^2$, the applied gray polyurethane coating liquid was dried to prepare a gray processed woven fabric. The processed woven fabric prepared was such that it reflects heat rays of direct sunlight and can be used for uses such as a tent that prevents temperature rise. In addition, after the prepared white polyurethane coating liquid was applied as undercoating, the undercoating was top-coated with the prepared black polyurethane coating liquid to obtain a polyurethane synthetic leather having a two-layered structure. The obtained synthetic leather was such that it reflects heat rays and can be used for uses such as interior decoration of an automobile.

Production and Evaluation (1) of Spun-Dyed Fiber

Example 1-18

A powdery colorant (dry color) having a pigment content of 50% was obtained by mixing 50 parts of the micronized powder of the black pigment obtained in Example 1-7, 2.5 parts of the pigment dispersant (A) obtained in Example 1-1, and 50 parts of a lubricant (ethylenebisstearamide powder) using a Henschel mixer. After 1 part of the obtained dry color and 99 parts of polypropylene resin pellets were mixed using a Henschel mixer, a resultant mixture was kneaded using a bent type 40 m/m extruder to obtain resin pellets containing 0.5% of the black pigment. The obtained resin pellets were spun using a melt-spinning machine to obtain a clear black polypropylene fiber (spun-dyed fiber) having an excellent pigment dispersibility and having a fineness of 10 deniers. A woven fabric prepared using the spun-dyed fiber obtained was such that it can reflect heat rays of direct sunlight and can be used for uses such as a parasol or a curtain that avoids temperature rise.

Production and Evaluation (1) of Resin-Shaped Article

Example 1-19

A dry color was obtained by mixing 5 parts of the micronized powder of the black pigment obtained in Example 1-7, 0.1 parts of the pigment dispersant (A) obtained in Example 1-1, 20 parts of a titanium oxide white pigment, and 75 parts of a polyethylene resin powder using a Henschel mixer. After 1 part of the obtained dry color and 100 parts of polybutylene terephthalate (PBT) resin pellets were mixed using a Henschel mixer, a resultant mixture was kneaded using an extruder to obtain black resin pellets. The obtained resin pellets were shaped using an in-line screw extrusion shaping machine to obtain a black resin-shaped plate having an excellent pigment dispersibility. The resin-shaped plate obtained was such that it can reflect heat rays of direct sunlight and can be used as a resin shaped article that avoids temperature rise.

Production and Evaluation (1) of Printing Paste for Woven Fabric

Example 1-20

Preliminary mixing was performed sufficiently on 71 parts of a press cake containing 25 parts of the micronized powder of the black pigment obtained in Example 1-7, 1.5 parts of the pigment dispersant (A) obtained in Example 1-1, 10 parts of a nonionic pigment dispersant, 1 part of a defoamer, and 18 parts of water. Subsequently, the pigment was dispersed using a horizontal type continuous medium disperser, which uses a glass bead as a dispersion medium, to prepare a high-concentration dispersion liquid of the black pigment (black color base). Emulsification dispersion was performed on 20 parts of the prepared black color base, 25 parts of a reactive acrylic acid alkyl ester latex (solid content of 40%), 0.5 parts of a defoamer, 1 part of a dispersant, 3 parts of a dispersion stabilizer for oil-in-water type emulsification, 38 parts of mineral turpentine, and 12.5 parts of water using a homogenizer (powerful emulsification disperser) to obtain an oil-in-water type black emulsion paste. To the obtained black emulsion paste, 2 parts of a carbodiimide-based crosslinking agent (solid content of 40%) was added, and a resultant mixture was mixed sufficiently to obtain a black printing paste. After the obtained black printing paste was printed on the whole surface of a polyester-cotton blended fabric, curing was performed at 120° C. for 15 minutes to obtain a black solid-printed fabric. The obtained solid-printed fabric was such that it can reflect heat rays.

Preparation (2) of Pigment Dispersants

Example 2-1

A solution was prepared by dissolving 30.5 parts of N-(4-methoxyphenyl)-2-hydroxy-11H-benzo[a]carbazole-3-carboxamide and 6.4 parts of sodium hydroxide in 800 parts of methanol. On the other hand, 13.9 parts of o-aminobenzenesulfonic acid was diazotized by an ordinary method to obtain a solution of a diazonium salt. The solution of the diazonium salt was added to the prepared solution to perform a coupling reaction at 20 to 30° C. for 5 hours. After filtration and washing with water were performed, drying was performed to obtain 43 parts of a blue-violet pigment dispersant (H) represented by the following formula (H).

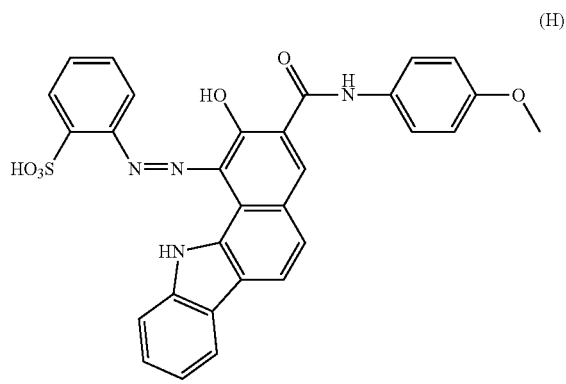 [SMILES: COc1ccc(NC(=O)c2cc3ccc4c5ccccc5[nH]c4c3c(N=Nc3ccccc3S(=O)(=O)O)c2O)cc1]

(H)

A peak of a molecular weight of 566.60 was detected by mass analysis using MALDI (Matrix Assisted Laser Desorption/Ionization). In addition, the purity measured using high-performance liquid chromatography (MODEL 860-CO (manufactured by JASCO Corporation), column: YMC Pack Pro C18 (manufactured by YMC CO., LTD.)) was 96%.

It was ascertained from the raw materials used, the result of mass analysis, and the result of high-performance liquid chromatography that a compound having an intended structure was obtained.

Example 2-2

A blue-violet pigment dispersant (I) represented by the following formula (I) in an amount of 42 parts was obtained in the same manner as in Example 2-1 described previously, except that 13.9 parts of m-aminobenzenesulfonic acid was used in place of 13.9 parts of o-aminobenzenesulfonic acid.

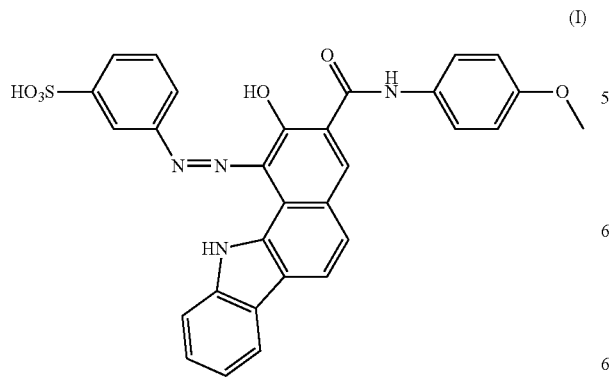

(I)

A peak of a molecular weight of 566.60 was detected by mass analysis using MALDI. In addition, the purity measured using high-performance liquid chromatography was 95%. It was ascertained from the raw materials used, the result of mass analysis, and the result of high-performance liquid chromatography that a compound having an intended structure was obtained.

Example 2-3

A blue-violet pigment dispersant (J) represented by the following formula (J) in an amount of 46 parts was obtained in the same manner as in Example 2-1 described previously, except that 17.9 parts of 4-amino-1-naphthalenesulfonic acid was used in place of 13.9 parts of o-aminobenzenesulfonic acid.

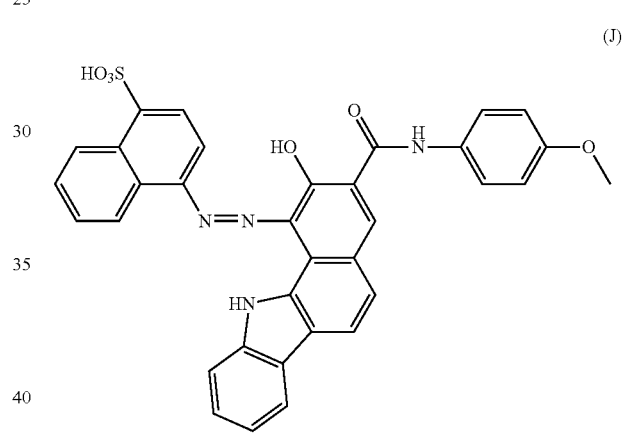

(J)

A peak of a molecular weight of 616.66 was detected by mass analysis using MALDI. In addition, the purity measured using high-performance liquid chromatography was 94%. It was ascertained from the raw materials used, the result of mass analysis, and the result of high-performance liquid chromatography that a compound having an intended structure was obtained.

Example 2-4

A blue-violet pigment dispersant (K) represented by the following formula (K) in an amount of 44 parts was obtained in the same manner as in Example 2-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide.

(K)

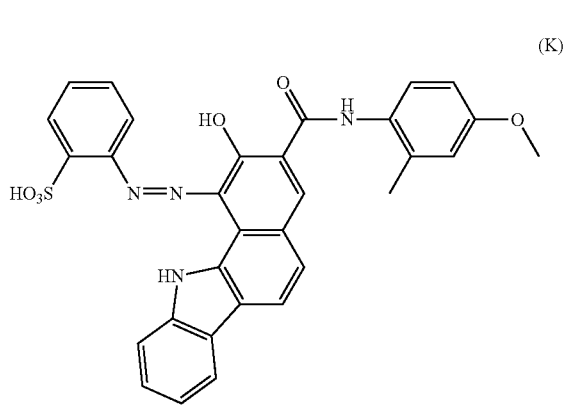 [SMILES: COc1ccc(NC(=O)c2cc3ccc4c5ccccc5[nH]c4c3c(N=Nc3ccccc3S(=O)(=O)O)c2O)c(C)c1]

A peak of a molecular weight of 580.62 was detected by mass analysis using MALDI. In addition, the purity measured using high-performance liquid chromatography was 94%. It was ascertained from the raw materials used, the result of mass analysis, and the result of high-performance liquid chromatography that a compound having an intended structure was obtained.

Example 2-5

A blue-violet pigment dispersant (L) represented by the following formula (L) in an amount of 45 parts was obtained in the same manner as in Example 2-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide, and 13.9 parts of m-aminobenzenesulfonic acid was used in place of 13.9 parts of o-aminobenzenesulfonic acid.

(L)

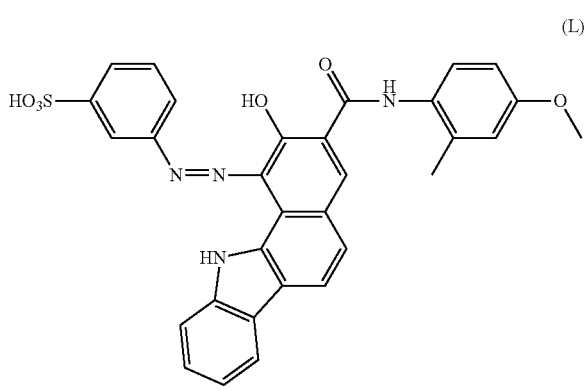 [SMILES: COc1ccc(NC(=O)c2cc3ccc4c5ccccc5[nH]c4c3c(N=Nc3cccc(S(=O)(=O)O)c3)c2O)c(C)c1]

A peak of a molecular weight of 580.62 was detected by mass analysis using MALDI. In addition, the purity measured using high-performance liquid chromatography was 94%. It was ascertained from the raw materials used, the result of mass analysis, and the result of high-performance liquid chromatography that a compound having an intended structure was obtained.

Example 2-6

A blue-violet pigment dispersant (M) represented by the following formula (M) in an amount of 48 parts was obtained in the same manner as in Example 2-1 described previously, except that 31.7 parts of N-(2-methyl-4-methoxyphenyl)-2-hydroxy-11H-benzo[a]carbazole-3-carboxamide was used in place of 30.5 parts of N-(4-methoxyphenyl)-2-hydroxy-11H-benzo[a]carbazole-3-carboxamide, and 17.9 parts of 4-amino-1-naphthalenesulfonic acid was used in place of 13.9 parts of o-aminobenzenesulfonic acid.

(M)

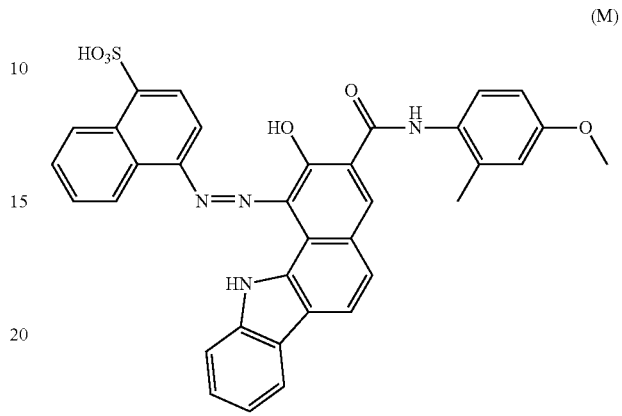

A peak of a molecular weight of 630.68 was detected by mass analysis using MALDI. In addition, the purity measured using high-performance liquid chromatography was 94%. It was ascertained from the raw materials used, the result of mass analysis, and the result of high-performance liquid chromatography that a compound having an intended structure was obtained.

Preparation (2) of Black Pigment Dispersion Liquids

Example 2-7

[Preparation of Micronized Powder of Black Pigment]

In a kneader to which a pressurization lid is installed, 100 parts of a black pigment (black azo pigment, trade name "CHROMOFINE BLACK A 1103", manufactured by Dainichiseika Color & Chemicals MFG. Co., Ltd.), 500 parts of a sodium chloride powder, and 50 parts of diethylene glycol were loaded. After preliminary mixing was performed until a uniformly wet lump was produced, the pressurization lid was closed, and the contents were kneaded and ground for 2 hours while pressurizing at a pressure of 6 kg/cm$^2$ and controlling the temperature in such a way as to be 92 to 98° C. After a ground product obtained was put into 3,000 parts of water warmed to 80° C., and a resultant mixture was stirred for 1 hour, filtration and washing with water were performed to remove sodium chloride and diethylene glycol, thereby obtaining a press cake. After a nonionic surfactant (in an amount of 200% to the pigment) was added to the obtained press cake, and a resultant mixture was diluted with water, an ultrasonic dispersion treatment was performed to prepare a pigment dispersion liquid. The average particle diameter of fine particles in the pigment dispersion liquid, as measured using a particle size distribution measurement device (trade name "Model N-4", manufactured by Beckman Coulter, Inc.), was about 90 nm. The press cake was dried and pulverized to obtain a micronized powder of the black pigment.

[Preparation of Black Pigment Dispersion Liquids]

Mixing was performed on 25 parts of the micronized powder of the black pigment, 1.5 parts of the pigment dispersant (H) obtained in Example 2-1, 10 parts of a benzyl methacrylate/methacrylic acid/2-hydroxyethyl methacrylate copolymer (molar ratio: 60/20/20, weight average molecular weight of 30,000), 5.5 parts of an basic polymer dispersant (trade name "DISPER BYK-2001", manufactured by BYK-Chemie GmbH, solid content of 46%), and 65 parts of propylene glycol-1-monomethyl ether-2-acetate. A resultant mixture was premixed and was then subjected to a dispersion treatment using a horizontal type bead mill to obtain a black pigment dispersion liquid (Example 2-7).

Examples 2-8 to 2-12

Black pigment dispersion liquids (Examples 2-8 to 2-12) were each obtained in the same manner as in Example 2-7 described previously, except that the pigment dispersants (I) to (M) were each used in place of the pigment dispersant (H).

Comparative Example 2-1

A black pigment dispersion liquid (Comparative Example 2-1) was obtained in the same manner as in Example 2-7 described previously, except that the pigment dispersant (H) was not used.

Comparative Example 2-2

A black pigment dispersion liquid (Comparative Example 2-2) was obtained in the same manner as in Example 2-7 described previously, except that a pigment dispersant (N) (sulfonated product of phthalocyanine (trade name "SOL-SPERS-12000" manufactured by The Lubrizol Corporation)) was used in place of the pigment dispersant (H).

<Evaluation (2)>

(1) Fluidity (storage stability), (2) gloss of colored surface, and (3) foreign substances in coating film were evaluated for each of the obtained black pigment dispersion liquids. Evaluation methods are described below. In addition, evaluation results are shown in Table 2.

(1) Fluidity (Storage Stability)

The viscosities (mPa·s) of the black pigment dispersion liquids were measured immediately after preparation (initial) and after leaving the black pigment dispersion liquids to stand at 25° C. for 1 month (after leaving black pigments to stand) using an E type viscometer. The measurement conditions were such that the temperature: room temperature (25° C.) and the number of revolutions of the rotor: 6 rpm. "Viscosity after leaving pigment dispersion liquid to stand/initial viscosity (%)" was calculated, and the "storage stability" was evaluated according to the evaluation criteria described below.

Good: "Viscosity after leaving pigment dispersion liquid to stand/initial viscosity" is 110% or less
Poor: "Viscosity after leaving pigment dispersion liquid to stand/initial viscosity" exceeds 110%

(2) Gloss of Colored Surface

The black pigment dispersion liquids were each applied on a polypropylene film using a bar coater (thickness of winding wire of 0.45 mm) to form a colored surface. The gloss of the colored surface formed was observed visually and was also observed using a gloss meter to evaluate the "gloss of colored surface" according to the evaluation criteria described below. It is to be noted that the higher the gloss of a colored surface, the more satisfactory the gloss of the colored surface can be determined.

Excellent: very satisfactory
Good: satisfactory
Poor: not satisfactory (3) Foreign Substances in Coating Film The black pigment dispersion liquids were each applied on a glass substrate using a spinner. Drying was performed at 90° C. for 2 minutes, and heating was then performed at 230° C. for 30 minutes to obtain coating films. The surfaces (applied surfaces) of the formed coating films were observed using a microscope (200 magnifications) to check whether foreign substances existed or not, and the "foreign substances in coating film" was evaluated according to the criteria described below.

Excellent: foreign substances do not exist
Good: slight amounts of foreign substances exist
Poor: foreign substance exist

TABLE 2

Main compositions and evaluation results of black pigment dispersion liquids

| Black pigment dispersion liquid | Pigment dispersant | Viscosity (mPa · s) Initial | Viscosity (mPa · s) After leaving black pigment dispersion liquid to stand | Viscosity after leaving black pigment dispersion liquid to stand/ initial viscosity (%) | Storage stability | Gloss of colored surface | Foreign substances in coating film |
|---|---|---|---|---|---|---|---|
| Comparative Example 2-1 | — | 163 | Gelation | — | Poor | Poor | Poor |
| Comparative Example 2-2 | N | 22 | 29 | 132 | Poor | Good | Good |
| Example 2-7 | H | 10 | 10.5 | 105 | Good | Excellent | Excellent |
| Example 2-8 | I | 11 | 11.5 | 105 | Good | Excellent | Excellent |
| Example 2-9 | J | 11 | 11 | 100 | Good | Excellent | Excellent |
| Example 2-10 | K | 12 | 12.5 | 104 | Good | Excellent | Excellent |
| Example 2-11 | L | 12 | 13 | 108 | Good | Excellent | Excellent |
| Example 2-12 | M | 12 | 12.5 | 104 | Good | Excellent | Excellent |

Formation and Evaluation (2) of BM Pattern of CF

Example 2-13

(1) Preparation of Photosensitive Black Resist Ink>

Compounded were 40 parts of the black pigment dispersion liquid obtained in Example 2-7, 5 parts of a propylene glycol-1-monomethyl ether-2-acetate solution containing 60% of an acrylated acrylic polyol photosensitive resin, 2 parts of trimethylolpropane triacrylate, 3 parts of dipentaerythritol hexaacrylate, 1 part of a photopolymerization initiator (ethanone-1-[9-ethyl-6-(2-methylbenzoyl)-9H-carbazole-3-yl]-1-(O-acetyl oxime), trade name "Irgacure OXE02", manufactured by BASF SE), and 51 parts of propylene glycol-1-monomethyl ether-2-acetate. After a resultant mixture was stirred sufficiently in such a way as to be uniform using a high-speed stirrer, filtration was performed with a filter having a pore diameter of 3 μm to prepare a photosensitive black resist ink.

(2) Evaluation of Black Coating Film (Resist Film)

The photosensitive black resist ink was applied on a glass substrate using a spin coater. After preliminary drying was performed at 60° C., pre-baking was performed. After exposure was performed in a light quantity of 400 mJ/cm using an ultrahigh pressure mercury lamp, post-baking was performed at 230° C. for 30 minutes to form a black coating film having a thickness of 2 μm. The light transmittance of the formed black coating film from the longer wavelength side of a visible light region to around 670 nm was 20% or less, the light transmittance at 780 nm reached 82%, and the light transmittance increases gradually from 780 nm to reach an equilibrium state. The light transmittance from around 580 to around 625 nm in particular was extremely low, as low as 5% or less. In addition, the volume resistivity of the formed black coating film was $10^{14}$ Ω·cm or more, so that the formed coating film was found to be a high insulation coating film.

(3) Formation of BM Pattern

After the photosensitive black resist ink was applied on a glass substrate using a spin coater, pre-baking was performed at 80° C. for 10 minutes to form a black coating film having a thickness of 2 μm. Exposure was performed through a negative photomask pattern of a BM pattern in a light quantity of 100 mJ/cm using an ultrahigh pressure mercury lamp. After development was performed with an alkaline developing solution, washing with water and drying were performed to form a BM pattern (BM film). The formed BM film is a high insulation coating film and therefore can be used, for example, as a BM film that keeps the thickness of a liquid crystal layer in place of a spacer and can construct a liquid crystal of the IPS type, the COA type, or the like. In addition, the formed BM film sufficiently absorbs visible light up to a longer wavelength region and therefore can suitably be used as BM of a LCD panel that adopts a LED back light.

(4) Preparation of Red, Green, Blue, Yellow, and Violet Pigment Dispersion Liquids Each color pigment dispersion liquid was prepared in the same manner as in Example 2-7 described previously, except that each of PR 254 (diketopyrrolopyrrole red pigment), PR 177 (anthraquinone-based red pigment), PG 36 (copper phthalocyanine green pigment), PB 15:6 (e type copper phthalocyanine blue pigment), PY 185 (yellow pigment), and PV 23 (dioxazine violet pigment) was used in place of CHROMOFINE BLACK A 1103, and a known pigment derivative having a sulfonate group was used.

(5) Preparation of Each Color Photosensitive Resist Ink

A compounded product was obtained by compounding the pigment dispersion liquid in which PR 254 was used and the pigment dispersion liquid in which PR 177 was used in a ratio of 8:2. A photosensitive red resist ink was prepared in the same manner as in the case of the photosensitive black resist ink described previously, except that the compounded product obtained was used in place of the black pigment dispersion liquid.

In addition, a compounded product was obtained by compounding the pigment dispersion liquid in which PG 36 was used and the pigment dispersion liquid in which PY 185 was used in a ratio of 6:4. A photosensitive green resist ink was prepared in the same manner as in the case of the photosensitive black resist ink described previously, except that the compounded product obtained was used in place of the black pigment dispersion liquid.

Further, a compounded product was obtained by compounding the pigment dispersion liquid in which PB 15:6 was used and the pigment dispersion liquid in which PV 23 was used in a ratio of 8:2. A photosensitive blue resist ink was prepared in the same manner as in the case of the photosensitive black resist ink described previously, except that the compounded product obtained was used in place of the black pigment dispersion liquid.

(6) Formation of RGB Pixels of CF

The glass substrate having BM formed thereon was set in a spin coater. After the glass substrate was spin-coated with the prepared photosensitive red resist ink, pre-baking was performed at 80° C. for 10 minutes. Exposure was performed through a photomask having a mosaic pattern in a light quantity of 100 mJ/cm$^2$ using a proximity exposure machine equipped with an ultrahigh pressure mercury lamp. After development and washing were performed using a dedicated developing solution and a dedicated rinse, drying was performed to form a mosaic red pattern on the glass substrate. A mosaic green pattern and a mosaic blue pattern were formed in the same manner as described above, except that the photosensitive green resist ink and the photosensitive blue resist ink were used respectively in place of the photosensitive red resist ink. Thereby, CF having BM and RGB pixels each formed thereon was obtained. The obtained CF was such that it exhibits excellent CF properties.

Preparation and Evaluation (2) of Gravure Printing Ink

Example 2-14

Mixing was performed on 10.5 parts of the micronized powder of the black pigment obtained in Example 2-7, 0.5 parts of the pigment dispersant (H) obtained in Example 2-1, and 30 parts of a methyl ethyl ketone:toluene (1:3) mixed solvent solution containing 40% of a polyurethane resin obtained by chain-extending a polyester having an isocyanate at an end thereof with a diamine. After 2 parts of a cationic polymer dispersant, 2.5 parts of a toluene solution containing 40% of a polycarbodiimide compound obtained using tolylene diisocyanate, and 54.5 parts of a methyl ethyl ketone:toluene:isopropyl alcohol (50:30:20) mixed solvent were added, a resultant mixture was mixed sufficiently using a high-speed stirrer. The pigment was dispersed using a horizontal type continuous medium disperser, which uses a glass bead as a dispersion medium, to prepare a black gravure printing ink. Black films were obtained by applying the prepared gravure ink on a polyamide film, a polyester film, and a polypropylene film using a gravure printing machine, thereby perform printing. All the obtained black films were such that they can shield visible light and sufficiently transmit near infrared rays.

Production and Evaluation (2) of Polycarbonate Resin-Shaped Plate

Example 2-15

Mixing was performed sufficiently on 20 parts of the micronized powder of the black pigment obtained in Example 2-7, 1 part of the pigment dispersant (H) obtained in Example 2-1, and 80 parts of a polycarbonate resin powder using a Henschel mixer. Subsequently, a resultant mixture was mixed and kneaded using a twin-screw extruder to obtain a master batch containing 20% of the black pigment. After 2 parts of the obtained master batch and 100 parts of polycarbonate resin pellets were mixed using a Henschel mixer, a resultant mixture was kneaded using a twin-screw extruder to obtain black resin pellets. The obtained resin pellets were shaped using an in-line screw injection shaping machine to obtain a black polycarbonate resin-shaped plate (black plate) which is excellent in pigment dispersibility. The obtained black plate was such that it shields visible light and sufficiently transmits near infrared rays, and therefore can be used for uses such as an infrared ray transmission filter.

Production and Evaluation (2) of Acrylic Resin-Shaped Plate

Example 2-16

Mixing was performed sufficiently on 20 parts of the micronized powder of the black pigment obtained in Example 2-7, 1 part of the pigment dispersant (H) obtained in Example 2-1, and 80 parts of an acrylic resin (polymethyl methacrylate) powder using a Henschel mixer. Subsequently, a resultant mixture was mixed and kneaded using a twin-screw extrusion kneader to obtain a master batch containing 20% of the black pigment. After 2 parts of the obtained master batch and 100 parts of acrylic resin pellets were mixed using a Henschel mixer, a resultant mixture was kneaded using an extruder to obtain black resin pellets. The obtained resin pellets were shaped using an in-line screw injection shaping machine to obtain a black acrylic resin-shaped plate (black plate) which is excellent in pigment dispersibility. The obtained black plate was such that it shields visible light and sufficiently transmits near infrared rays, and therefore can be used for uses such as an infrared ray transmission filter.

Preparation and Evaluation (2) of Polyurethane Coating Agent

Example 2-17

(1) Preparation of Polyurethane Coating Agent (Liquid)

Kneading was performed sufficiently on 40 parts of the micronized powder of the black pigment obtained in Example 2-7, 2 parts of the pigment dispersant (H) obtained in Example 2-1, and 60 parts of an adipic acid ester-based plasticizer using a three-roll kneader to obtain a plasticizer-dispersed paste of the black pigment (black pigment toner). In addition, 60 parts of a titanium oxide white pigment and 40 parts of an adipic acid ester-based plasticizer were kneaded sufficiently using a three-roll kneader to obtain a plasticizer-dispersed paste of the white pigment (white pigment toner). On the other hand, 100 parts of a methyl ethyl ketone dispersion liquid (solid content: 30%) of a polyether polyol/diphenylmethane diisocyanate-based polyurethane having a carboxy group, 5 parts of a methyl ethyl ketone solution (solid content: 50%) of a polyether polyol/diphenylmethane diisocyanate-based polyurethane, and 2.5 parts of a polycarbodiimide-based crosslinking agent (solid content: 20%) were mixed sufficiently to obtain a mixture. After 1 part of the black pigment toner and 6 parts of the white pigment toner were added to the obtained mixture, a resultant mixture was mixed sufficiently to prepare a gray polyurethane coating liquid.

In addition, a white polyurethane coating liquid was prepared in the same manner as described above, except that the black pigment toner was not used and only the white pigment toner was used. Further, a black polyurethane coating liquid was prepared in the same manner as described above, except that the white pigment toner was not used and only the black pigment toner was used.

(2) Evaluation

After the prepared gray polyurethane coating liquid was applied on the surface of tent cloth of a nylon woven fabric in such a way as to be about 200 g/m$^2$, the applied gray polyurethane coating liquid was dried to prepare a gray processed woven fabric. The processed woven fabric prepared was such that it reflects heat rays of direct sunlight and can be used for uses such as a tent that prevents temperature rise. In addition, after the prepared white polyurethane coating liquid was applied as undercoating, the undercoating was top-coated with the prepared black polyurethane coating liquid to obtain a polyurethane synthetic leather having a two-layered structure. The obtained synthetic leather was such that it reflects heat rays and can be used for uses such as interior decoration of an automobile.

Production and Evaluation (2) of Spun-dyed Fiber

Example 2-18

A powdery colorant (dry color) having a pigment content of 50% was obtained by mixing 50 parts of the micronized powder of the black pigment obtained in Example 2-7, 2.5 parts of the pigment dispersant (H) obtained in Example 2-1, and 50 parts of a lubricant (ethylenebisstearamide powder) using a Henschel mixer. After 1 part of the obtained dry color and 99 parts of polypropylene resin pellets were mixed using a Henschel mixer, a resultant mixture was kneaded using a bent type 40 m/m extruder to obtain resin pellets containing 0.5% of the black pigment. The obtained resin pellets were spun using a melt-spinning machine to obtain a clear black polypropylene fiber (spun-dyed fiber) having an excellent pigment dispersibility and having a fineness of 10 deniers. A woven fabric prepared using the spun-dyed fiber obtained was such that it can reflect heat rays of direct sunlight and can be used for uses such as a parasol or a curtain that avoids temperature rise.

Production and Evaluation (2) of Resin-shaped Article

Example 2-19

A dry color was obtained by mixing 5 parts of the micronized powder of the black pigment obtained in Example 2-7, 0.1 parts of the pigment dispersant (H) obtained in Example 2-1, 20 parts of a titanium oxide white pigment, and 75 parts of a polyethylene resin powder using a Henschel mixer. After 1 part of the obtained dry color and 100 parts of polybutylene terephthalate (PBT) resin pellets were mixed using a Henschel mixer, a resultant mixture was kneaded using an extruder to obtain black resin pellets. The obtained resin pellets were shaped using an in-line screw extrusion shaping machine to obtain a black resin-shaped plate having an excellent pigment dispersibility. The resin-shaped plate obtained was such that it can reflect heat rays of direct sunlight and can be used as a resin-shaped article that avoids temperature rise.

Production and Evaluation (2) of Printing Paste for Woven Fabric

Example 2-20

Preliminary mixing was performed sufficiently on 71 parts of a press cake containing 25 parts of the micronized powder of the black pigment obtained in Example 2-7, 1.5 parts of the pigment dispersant (H) obtained in Example 2-1, 10 parts of a nonionic pigment dispersant, 1 part of a defoamer, and 18 parts of water. Subsequently, the pigment was dispersed using a horizontal type continuous medium disperser, which uses a glass bead as a dispersion medium, to prepare a high-concentration dispersion liquid of the black pigment (black color base). Emulsification dispersion was performed on 20 parts of the prepared black color base, 25 parts of a reactive acrylic acid alkyl ester latex (solid content of 40%), 0.5 parts of a defoamer, 1 part of a dispersant, 3 parts of a dispersion stabilizer for oil-in-water type emulsification, 38 parts of mineral turpentine, and 12.5 parts of water using a homogenizer (powerful emulsification disperser) to obtain an oil-in-water type black emulsion paste. To the obtained black emulsion paste, 2 parts of a carbodiimide-based crosslinking agent (solid content of 40%) was added, and a resultant mixture was mixed sufficiently to obtain a black printing paste. After the obtained black printing paste was printed on the whole surface of a polyester-cotton blended fabric, curing was performed at 120° C. for 15 minutes to obtain a black solid-printed fabric. The obtained solid-printed fabric was such that it can reflect heat rays.

The invention claimed is:

1. A pigment dispersant being a compound represented by following formula (1):

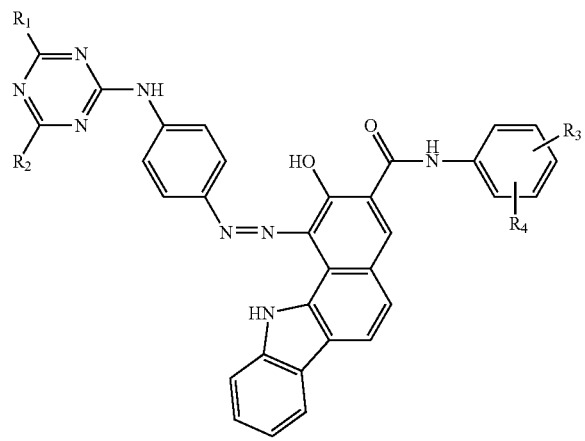

(1)

wherein $R_1$ and $R_2$ each independently represent a group obtained by eliminating one hydrogen atom from an amino group of an amine compound having a chain or cyclic aliphatic hydrocarbon group having 2 to 30 carbon atoms or an aromatic hydrocarbon group, the amine compound containing a basic nitrogen atom and optionally containing a hetero atom other than a nitrogen atom, and $R_3$ and $R_4$ each independently represent a hydrogen atom, a halogen atom, an alkyl group, an alkoxy group, or a hydroxy group.

2. The pigment dispersant according to claim 1, wherein $R_1$ and $R_2$ in the formula (1) each independently represent a group represented by following formula (2) or (3):

(2)

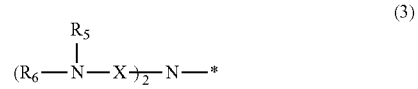

(3)

wherein * shows a position of bonding with a triazine ring; each X independently represents an alkylene group having 1 to 4 carbon atoms; and $R_5$ and $R_6$ each independently represent a hydrogen atom or an alkyl group having 1 to 6 carbon atoms, $R_5$ and $R_6$ optionally bond to each other to form a cyclic structure, and the cyclic structure optionally contains a hetero atom.

3. A pigment composition comprising:

a pigment; and the pigment dispersant according to claim 1.

4. The pigment composition according to claim 3, wherein a content of the pigment dispersant based on 100 parts by mass of the pigment is in a range from 0.5 to 40 parts by mass.

5. A pigment colorant comprising:

the pigment composition according to claim 3; and a film-forming material.

6. The pigment colorant according to claim 5 for displaying images, recording images, a gravure printing ink, a writing ink, a plastic, pigment printing, a paint, or a black matrix of a color filter.

* * * * *